US009782570B2

(12) United States Patent
Hirszowicz et al.

(10) Patent No.: US 9,782,570 B2
(45) Date of Patent: Oct. 10, 2017

(54) BALLOON CATHETER

(71) Applicant: AngioSlide Ltd., Natania (IL)

(72) Inventors: Eran Hirszowicz, Ramat-Gan (IL); Shay Dubi, Tel-Aviv (IL)

(73) Assignee: AngioSlide Ltd., Natania (IL)

( * ) Notice: Subject to any disclaimer, the term of this patent is extended or adjusted under 35 U.S.C. 154(b) by 194 days.

(21) Appl. No.: 14/551,866

(22) Filed: Nov. 24, 2014

(65) Prior Publication Data
US 2015/0126966 A1 May 7, 2015

Related U.S. Application Data

(63) Continuation of application No. 12/083,436, filed as application No. PCT/IB2006/002955 on Oct. 13, 2006, now Pat. No. 8,894,680, which is a continuation of application No. 11/477,812, filed on Jun. 30, 2006, now Pat. No. 8,556,851.
(Continued)

(51) Int. Cl.
*A61M 25/10* (2013.01)
*A61M 25/01* (2006.01)

(52) U.S. Cl.
CPC .... *A61M 25/1006* (2013.01); *A61M 25/0119* (2013.01); *A61M 25/104* (2013.01); *A61M 2025/0183* (2013.01); *A61M 2025/109* (2013.01); *A61M 2025/1015* (2013.01); *A61M 2025/1068* (2013.01)

(58) Field of Classification Search
CPC .. A61M 2025/0183; A61M 2025/1015; A61M 2025/1068; A61M 2025/109; A61M 25/0119; A61M 25/1006; A61M 25/104
See application file for complete search history.

(56) References Cited

U.S. PATENT DOCUMENTS 4,004,588 A 1/1977 Alexander
4,243,040 A 1/1981 Beecher
(Continued)

FOREIGN PATENT DOCUMENTS

CA 2183214 2/1998
CN 1322145 11/2001
(Continued)

OTHER PUBLICATIONS

Communication Under Rule 71(3) EPC Dated Mar. 24, 2012 From the European Patent Office Re. Application No. 09773059.2.
(Continued)

*Primary Examiner* — Julie A Szpira

(57) ABSTRACT

A rapid exchange balloon catheter including: an outer conduit having a lumen and a wall surrounding the lumen, the wall including a lateral opening formed therein; an inner conduit having a proximal end and a distal end; a sealing sleeve for sealing the lateral opening of the outer conduit; a balloon whose proximal margin is attached to the outer surface of the distal end of the outer conduit, and whose distal margin is attached to the outer surface of the portion of the inner conduit that extends beyond the distal end of the outer conduit; a pushing-pulling mechanism disposed in the outer conduit; and a fluid port for the introduction of an expansion fluid and for the removal of the expansion fluid.

20 Claims, 5 Drawing Sheets

Related U.S. Application Data

(60) Provisional application No. 60/726,160, filed on Oct. 14, 2005.

(56) References Cited

U.S. PATENT DOCUMENTS

| | | | |
|---|---|---|---|
| 4,271,839 A | 6/1981 | Fogarty et al. | |
| 4,469,100 A * | 9/1984 | Hardwick | A61B 17/22032 604/908 |
| 4,597,389 A | 7/1986 | Ibrahim | |
| 4,611,594 A | 9/1986 | Grayhack et al. | |
| 4,748,982 A | 6/1988 | Horzewski et al. | |
| 4,762,129 A | 8/1988 | Bonzel | |
| 4,820,270 A | 4/1989 | Hardcastle et al. | |
| 4,846,174 A | 7/1989 | Willard et al. | |
| 4,946,440 A * | 8/1990 | Hall | A61B 18/08 600/569 |
| 4,955,895 A | 9/1990 | Sugiyama et al. | |
| 4,968,300 A | 11/1990 | Moutafis et al. | |
| 5,019,041 A | 5/1991 | Robinson et al. | |
| 5,074,845 A | 12/1991 | Miraki et al. | |
| 5,092,839 A | 3/1992 | Kipperman | |
| 5,109,830 A | 5/1992 | Cho | |
| 5,254,091 A | 10/1993 | Allah Mad et al. | |
| 5,307,814 A | 5/1994 | Kressel et al. | |
| RE34,633 E | 6/1994 | Sos et al. | |
| 5,338,298 A | 8/1994 | McIyntire | |
| 5,421,826 A | 6/1995 | Crocker et al. | |
| 5,437,638 A | 8/1995 | Bowman | |
| 5,445,646 A | 8/1995 | Euteneuer et al. | |
| 5,470,314 A | 11/1995 | Walinsky | |
| 5,534,007 A | 7/1996 | St. Germain et al. | |
| 5,630,822 A | 5/1997 | Hermann et al. | |
| 5,785,675 A * | 7/1998 | Drasler | A61B 17/32037 604/22 |
| 5,865,801 A | 2/1999 | Houser | |
| 5,868,767 A | 2/1999 | Farley et al. | |
| 5,941,895 A | 8/1999 | Myler et al. | |
| 5,968,012 A | 10/1999 | Ren et al. | |
| 6,004,341 A | 12/1999 | Zhu et al. | |
| 6,022,359 A | 2/2000 | Frantzen | |
| 6,039,721 A | 3/2000 | Johnson et al. | |
| 6,063,057 A | 5/2000 | Choh | |
| 6,129,706 A | 10/2000 | Janacek | |
| 6,152,947 A | 11/2000 | Ambrisco et al. | |
| 6,159,230 A | 12/2000 | Samuels | |
| 6,179,827 B1 | 1/2001 | Davis et al. | |
| 6,280,412 B1 | 8/2001 | Pederson, Jr. et al. | |
| 6,383,195 B1 | 5/2002 | Richard | |
| 6,695,810 B2 * | 2/2004 | Peacock, III | A61B 17/00234 604/101.05 |
| 7,172,576 B2 | 2/2007 | Sawa et al. | |
| 7,201,770 B2 | 4/2007 | Johnson et al. | |
| 7,563,270 B2 * | 7/2009 | Gumm | A61F 2/856 604/96.01 |
| 7,591,831 B2 * | 9/2009 | Parsonage | A61F 2/01 523/113 |
| 7,824,345 B2 | 11/2010 | Euteneuer et al. | |
| 7,824,370 B2 | 11/2010 | Hirszowicz et al. | |
| 8,556,851 B2 | 10/2013 | Hirszowicz et al. | |
| 2002/0082639 A1 | 6/2002 | Broome et al. | |
| 2002/0091398 A1 | 7/2002 | Galdonik et al. | |
| 2002/0121472 A1 | 9/2002 | Garner et al. | |
| 2002/0177870 A1 | 11/2002 | Sepetka et al. | |
| 2003/0028211 A1 | 2/2003 | Crocker et al. | |
| 2003/0055483 A1 | 3/2003 | Gumm | |
| 2003/0093107 A1 | 5/2003 | Parsonage et al. | |
| 2003/0105508 A1 | 6/2003 | Johnson et al. | |
| 2003/0130672 A1 | 7/2003 | DoBrava et al. | |
| 2003/0176884 A1 | 9/2003 | Berrada et al. | |
| 2003/0176910 A1 | 9/2003 | Vrba et al. | |
| 2003/0208223 A1 | 11/2003 | Kleiner | |
| 2004/0049223 A1 | 3/2004 | Nishtala et al. | |
| 2004/0054362 A1 | 3/2004 | Lopath et al. | |
| 2004/0073243 A1 | 4/2004 | Sepetka et al. | |
| 2004/0236275 A1 * | 11/2004 | Pruitt | A61L 29/02 604/96.01 |
| 2004/0236367 A1 * | 11/2004 | Brown | A61M 25/10 606/194 |
| 2005/0004553 A1 * | 1/2005 | Douk | A61B 17/12022 604/523 |
| 2005/0085826 A1 | 4/2005 | Nair et al. | |
| 2005/0101986 A1 | 5/2005 | Daniel et al. | |
| 2005/0102019 A1 | 5/2005 | Yadin | |
| 2005/0137501 A1 | 6/2005 | Euteneuer et al. | |
| 2005/0137607 A1 | 6/2005 | Assell et al. | |
| 2005/0154414 A1 * | 7/2005 | Perreault | A61M 25/1006 606/192 |
| 2005/0187570 A1 | 8/2005 | Nguyen et al. | |
| 2005/0209629 A1 | 9/2005 | Kerr et al. | |
| 2005/0261705 A1 | 11/2005 | Gist | |
| 2005/0288700 A1 | 12/2005 | Chermoni | |
| 2006/0015134 A1 | 1/2006 | Trinidad | |
| 2006/0025720 A1 | 2/2006 | Sawa et al. | |
| 2006/0129107 A1 | 6/2006 | McArthur et al. | |
| 2006/0129710 A1 | 6/2006 | O'Connor et al. | |
| 2007/0083158 A1 | 4/2007 | Hirszowicz et al. | |
| 2007/0088380 A1 | 4/2007 | Hirszowicz et al. | |
| 2007/0255305 A1 | 11/2007 | McMichael et al. | |
| 2008/0051706 A1 | 2/2008 | Hirszowicz et al. | |
| 2009/0112239 A1 | 4/2009 | To | |
| 2009/0171278 A1 | 7/2009 | Hirszowicz et al. | |
| 2009/0204069 A1 | 8/2009 | Hirszowicz et al. | |
| 2009/0247945 A1 | 10/2009 | Levit et al. | |
| 2009/0270902 A1 | 10/2009 | Assell et al. | |
| 2010/0010303 A1 | 1/2010 | Bakos | |
| 2010/0016792 A1 | 1/2010 | Hirszowicz | |
| 2010/0022970 A1 | 1/2010 | Hirszowicz | |
| 2011/0040365 A1 | 2/2011 | Hirszowicz et al. | |
| 2011/0275990 A1 | 11/2011 | Besser et al. | |
| 2012/0302996 A1 | 11/2012 | Barash et al. | |
| 2013/0006291 A1 | 1/2013 | Harari et al. | |
| 2013/0060234 A1 | 3/2013 | Besser et al. | |
| 2015/0306361 A1 | 10/2015 | Feig et al. | |

FOREIGN PATENT DOCUMENTS

| | | |
|---|---|---|
| CN | 101583318 | 11/2009 |
| CN | 101972510 | 2/2011 |
| CN | 102131471 | 7/2011 |
| EP | 0 200 668 | 12/1986 |
| EP | 0 359 489 | 3/1990 |
| EP | 359489 | 3/1990 |
| EP | 0366478 | 5/1990 |
| EP | 0 380 873 | 8/1990 |
| EP | 0399712 | 11/1990 |
| EP | 0987045 | 3/2000 |
| EP | 1120129 | 8/2001 |
| EP | 1124504 | 8/2001 |
| EP | 1333778 | 11/2001 |
| EP | 1333778 | 8/2003 |
| EP | 1062966 | 9/2004 |
| EP | 1753348 | 2/2007 |
| GB | 2 054 385 | 2/1981 |
| IL | 178738 | 2/2007 |
| JP | 54-066582 | 5/1979 |
| JP | 59-502134 | 12/1984 |
| JP | 61-293474 | 12/1986 |
| JP | 02-119875 | 5/1990 |
| JP | 07-136283 | 5/1995 |
| JP | 2000005189 A | 1/2000 |
| JP | 2002-520099 | 7/2002 |
| JP | 2003-126263 | 5/2003 |
| JP | 2004-329485 | 11/2004 |
| JP | 2005-514979 | 5/2005 |
| WO | 84/01513 | 4/1984 |
| WO | WO 95/17223 | 6/1995 |
| WO | 98/29026 | 7/1998 |
| WO | 00/02613 | 1/2000 |
| WO | WO 00/27309 | 5/2000 |
| WO | 00/38776 | 7/2000 |
| WO | 02/38084 | 5/2002 |
| WO | WO 02/038084 | 5/2002 |

(56) References Cited

FOREIGN PATENT DOCUMENTS

| WO | 02/055146 | 7/2002 |
|---|---|---|
| WO | 2004/014240 | 2/2004 |
| WO | WO 2004/017865 | 3/2004 |
| WO | WO 2004/028611 | 4/2004 |
| WO | 2004/082462 | 9/2004 |
| WO | 2004/098681 | 11/2004 |
| WO | 2005/000130 | 1/2005 |
| WO | WO 2005/030308 | 4/2005 |
| WO | 2005/041788 | 5/2005 |
| WO | WO 2005/102184 | 11/2005 |
| WO | 2005/112783 | 12/2005 |
| WO | WO 2005/112783 | 12/2005 |
| WO | WO 2007/004221 | 1/2007 |
| WO | WO 2007/042935 | 4/2007 |
| WO | WO 2007/042936 | 4/2007 |
| WO | WO 2007/132464 | 11/2007 |
| WO | WO 2008/004238 | 1/2008 |
| WO | WO 2008/004239 | 1/2008 |
| WO | WO 2009/053839 | 4/2009 |
| WO | WO 2010/001404 | 1/2010 |
| WO | WO 2010/001405 | 1/2010 |
| WO | WO 2010/079494 | 7/2010 |
| WO | WO 2011/036667 | 3/2011 |
| WO | WO 2011/080731 | 7/2011 |
| WO | WO 2011/080732 | 7/2011 |
| WO | WO 2011/089599 | 7/2011 |
| WO | WO 2014/087395 | 6/2014 |
| WO | WO 2016/199117 | 12/2016 |

OTHER PUBLICATIONS

Communication Pursuant to Article 94(3) and Rule 71(1) EPC Dated Jan. 28, 2010 From the European Patent Office Re. Application No. 07766874.7.
Communication Pursuant to Article 94(3) EPC Dated Apr. 4, 2012 From the European Patent Office Re. Application No. 10170623.2.
Communication Pursuant to Article 94(3) EPC Dated Mar. 10, 2011 From the European Patent Office Re. Application No. 07766875.4.
Communication Pursuant to Article 94(3) EPC Dated Feb. 23, 2010 From the European Patent Office Re. Application No. 07766875.4.
Communication Pursuant to Article 94(3) EPC Dated Jan. 28, 2010 From the European Patent Office Re. Application No. 07766874.7.
Communication Pursuant to Article 94(3) EPC Dated Dec. 29, 2008 From the European Patent Office Re. Application No. 05735055.5.
Communication Pursuant to Article 94(3) EPC Dated May 29, 2008 From the European Patent Office Re. Application No. 06766111.6.
Communication Pursuant to Article 94(3) EPC Dated Aug. 30, 2011 From the European Patent Office Re. Application No. 10170623.2.
Communication Pursuant to Article 96(2) EPC Dated Nov. 5, 2007 From the European Patent Office Re. Application No. 05735055.5.
Communication Pursuant to Rules 161(2) and 162 EPC Dated May 3, 2012 From the European Patent Office Re. Application No. 10818501.8.
Communication Pursuant to Rules 161(2) and 162 EPC Dated Feb. 14, 2011 From the European Patent Office Re. Application No. 09773059.2.
Communication Pursuant to Rules 161(2) and 162 EPC Dated Feb. 14, 2011 From the European Patent Office Re. Application No. 09773060.0.
Communication Pursuant to Rules 161(2) and 162 EPC Dated Jul. 15, 2015 From the European Patent Office Re. Application No. 13861353.4.
Communication Pursuant to Rules 70(2) and 70a(2) EPC Dated Oct. 4, 2011 From the European Patent Office Re. Application No. 09773059.2.
Communication Under Rule 71(3) EPC Dated Jul. 6, 2009 From the European Patent Office Re. Application No. 06766111.6.
Communication Under Rule 71(3) EPC Dated Mar. 10, 2010 From the European Patent Office Re. Application No. 05735055.5.
Communication Under Rule 71(3) EPC Dated Mar. 16, 2012 From the European Patent Office Re. Application No. 10169255.6.
Communication Under Rule 71(3) EPC Dated Aug. 19, 2015 From the European Patent Office Re. Application No. 10170623.2.
Decision of Patent Dated Mar. 6, 2012 From the Japanese Patent Office Re. Application No. 2007-509059 and Its Translation Into English.
Decision to Grant a European Patent Pursuant to Article 97(1) EPC Dated Aug. 12, 2010 From the European Patent Office Re. Application No. 10170623.2.
Decision to Grant a European Patent Pursuant to Article 97(1) EPC Dated Aug. 17, 2012 From the European Patent Office Re. Application No. 10169255.6.
Decision to Grant a European Patent Pursuant to Article 97(1) EPC Dated Jul. 19, 2010 From the European Patent Office Re. Application No. 05735055.5.
European Search Report and the European Search Opinion Dated Nov. 15, 2010 From the European Patent Office Re. Application No. 10169255.6.
European Search Report and the European Search Opinion Dated Nov. 26, 2010 From the European Patent Office Re. Application No. 10170623.2.
Examiner's Report Dated Feb. 2, 2011 From the Australian Government, IP Australia Re. Application No. 2006264397.
Final Rejection Dated Aug. 30, 2011 From the Japanese Patent Office Re. Application No. 2007-509059 and Its Translation Into English.
International Preliminary Report on Patentability Dated Jul. 4, 2012 From the International Bureau of WIPO Re. Application No. PCT/IL2010/000002.
International Preliminary Report on Patentability Dated Jan. 5, 2011 From the International Bureau of WIPO Re. Application No. PCT/IL2009/000667.
International Preliminary Report on Patentability Dated Jan. 5, 2011 From the International Bureau of WIPO Re. Application No. PCT/IL2009/000668.
International Preliminary Report on Patentability Dated Apr. 7, 2007 From the International Bureau of WIPO Re. Application No. PCT/IL2007/000845.
International Preliminary Report on Patentability Dated Apr. 7, 2009 From the International Bureau of WIPO Re. Application No. PCT/IL2007/000844.
International Preliminary Report on Patentability Dated Jan. 9, 2008 From the International Bureau of WIPO Re. Application No. PCT/IL2006/000770.
International Preliminary Report on Patentability Dated Jun. 9, 2015 From the International Bureau of WIPO Re. Application No. PCT/IL2013/000089.
International Preliminary Report on Patentability Dated Mar. 10, 2009 From the International Bureau of WIPO Re. Application No. PCT/IB2006/002955.
International Preliminary Report on Patentability Dated Jul. 12, 2011 From the International Bureau of WIPO Re. Application No. PCT/IL2009/000667.
International Preliminary Report on Patentability Dated Jul. 24, 2012 From the International Bureau of WIPO Re. Application No. PCT/IL2011/000060.
International Preliminary Report on Patentability Dated Oct. 25, 2006 From the International Bureau of WIPO Re. Application No. PCT/IL2005/000420.
International Preliminary Report on Patentability Dated Mar. 27, 2012 From the International Bureau of WIPO Re. Application No. PCT/IL2010/000797.
International Search Report and the Written Opinion Dated Jun. 1, 2010 From the International Searching Authority Re. Application No. PCT/IL2010/000025.
international Search Report and the Written Opinion Dated Nov. 3, 2006 From the International Searching Authority Re. Application No. PCT/IL2006/000770.
International Search Report and the Written Opinion Dated May 7, 2010 From the International Searching Authority Re. Application No. PCT/IL2010/000001.

(56) References Cited

OTHER PUBLICATIONS

International Search Report and the Written Opinion Dated Aug. 11, 2008 From the International Searching Authority Re. Application No. PCT/IL2007/000844.
International Search Report and the Written Opinion Dated Aug. 11, 2008 From the International Searching Authority Re. Application No. PCT/IL2007/000845.
International Search Report and the Written Opinion Dated May 12, 2010 From the International Searching Authority Re. Application No. PCT/IL2010/000002.
International Search Report and the Written Opinion Dated Feb. 23, 2011 From the International Searching Authority Re. Application No. PCT/IL2010/000797.
International Search Report and the Written Opinion Dated May 23, 2011 From the International Searching Authority Re. Application No. PCT/IL2011/000060.
International Search Report and the Written Opinion Dated Mar. 26, 2014 From the International Searching Authority Re. Application No. PCT/IL2013/000089.
International Search Report and the Written Opinion Dated Oct. 28, 2009 From the International Searching Authority Re. Application No. PCT/IL2009/000667.
International Search Report and the Written Opinion Dated Oct. 28, 2009 From the International Searching Authority Re. Application No. PCT/IL2009/000668.
International Search Report and the Written Opinion Dated Jul. 29, 2005 From the International Searching Authority Re. Application No. PCT/IL2005/000420.
International Search Report and the Written Opinion Dated Oct. 29, 2008 From the International Searching Authority Re. Application No. PCT/IB2006/002955.
Invitation Pursuant to Article 94(3) and Rule 71(1) EPC Dated Dec. 19, 2013 From the European Patent Office Re. Application No. 10170623.2.
Notice of Allowance Dated Jul. 3, 2013 From the US Patent and Trademark Office Re. U.S. Appl. No. 13/001,433.
Notice of Allowance Dated May 6, 2014 From the US Patent and Trademark Office Re. U.S. Appl. No. 13/001,433.
Notice of Allowance Dated Nov. 8, 2012 From the US Patent and Trademark Office Re. U.S. Appl. No. 12/901,535.
Notice of Allowance Dated Jul. 9, 2012 From the US Patent and Trademark Office Re. U.S. Appl. No. 12/901,535.
Notice of Allowance Dated Nov. 12, 2013 From the US Patent and Trademark Office Re. U.S. Appl. No. 13/001,433.
Notice of Allowance Dated Jul. 23, 2014 From the US Patent and Trademark Office Re. U.S. Appl. No. 12/083,436.
Notice of Refusal Dated May 19, 2014 From the Israel Patent Office Re. Application No. 211022.
Notice of the Reason for Rejection Dated May 13, 2013 From the Korean Intellectual Property Office Re. Application No. 10-2008-7010935.
Notification of Grounds for Rejection Dated Aug. 16, 2011 From the Japanese Patent Office Re. Application No. 2008-519139 and Its Translation Into English.
Notification of Grounds for Rejection Dated Oct. 25, 2011 From the Japanese Patent Office Re. Application No. 2008-535127 and Its Translation Into English.
Notification of Office Action Dated Oct. 24, 2012 From the State Intellectual Property Office of the People's Republic of China Re. Application No. 200980132738.0.
Notification of the Decision to Grant a Patent Right for Patent for Invention Dated Mar. 6, 2013 From the Patent Office of the People's Republic of China Re. Application No. 201010224944.9 and Its Translation Into English.
Notification of the Decision to Grant a Patent Right for Patent for Invention Dated Apr. 20, 2010 From the Patent Office of the People's Republic of China Re. Application No. 200580020733.0 and Its Translation Into English.
Office Action and Search Report Dated Apr. 2, 2013 From the State Intellectual Property Office of the People's Republic of China Re. Application No. 201210018835.0 and Its Translation Into English.
Office Action and Search Report Dated Aug. 4, 2014 From the State Intellectual Property Office of the People's Republic of China Re. Application No. 201310193577.4 and Its Translation Into English.
Office Action and Search Report Dated Aug. 31, 2012 From the State Intellectual Property Office of the People's Republic of China Re. Application No. 201010224944.9 and Its Translation Into English.
Office Action Dated Sep. 2, 2014 From the State Intellectual Property Office of the People's Republic of China Re. Application No. 201210018835.0 and Its Translation Into English.
Office Action Dated Mar. 5, 2012 From the Israel Patent Office Re. Application No. 178738.
Office Action Dated Mar. 5, 2012 From the Israel Patent Office Re. Application No. 211022.
Office Action Dated Jun. 6, 2012 From the Israel Patent Office Re. Application No. 211023.
Office Action Dated Mar. 6, 2012 From the State Intellectual Property Office of the People's Republic of China Re. Application No. 200680032507.9 and Its Translation Into English.
Office Action Dated Oct. 8, 2012 From the State Intellectual Property Office of the People's Republic of China Re. Application No. 200680047235.X and Its Translation Into English.
Office Action Dated Nov. 9, 2009 From the Israel Patent Office Re. Application No. 178738.
Office Action Dated Aug. 12, 2011 From the State Intellectual Property Office of the People's Republic of China Re. Application No. 200680032507.9 and Its Translation Into English.
Office Action Dated Jan. 12, 2012 From the State Intellectual Property Office of the People's Republic of China Re. Application No. 201010224944.9 and Its Translation Into English.
Office Action Dated Jun. 12, 2009 From the State Intellectual Property Office of the People's Republic of China Re. Application No. 200580020733.0 and Its Translation Into English.
Office Action Dated Apr. 13, 2015 From the State Intellectual Property Office of the People's Republic of China Re. Application No. 201310193577.4 and Its Translation Into English.
Office Action Dated Mar. 17, 2011 From the Israel Patent Office Re. Application No. 178738.
Office Action Dated Jun. 23, 2011 From the State Intellectual Property Office of the People's Republic of China Re. Application No. 201010224944.9 and Its Translation Into English.
Office Action Dated Oct. 23, 2009 From the State Intellectual Property Office of the People's Republic of China Re. Application No. 200680032507.9 and Its Translation Into English.
Office Action Dated Dec. 24, 2013 From the State Intellectual Property Office of the People's Republic of China Re. Application No. 201210018835.0 and Its Translation Into English.
Office Action Dated Oct. 25, 2011 From the State Intellectual Property Office of the People's Republic of China Re. Application No. 200680047235.X and Its Translation Into English.
Official Action Dated Dec. 5, 2011 From the US Patent and Trademark Office Re. U.S. Appl. No. 12/901,535.
Official Action Dated Dec. 8, 2009 From the US Patent and Trademark Office Re. U.S. Appl. No. 11/587,179.
Official Action Dated May 12, 2015 From the US Patent and Trademark Office Re. U.S. Appl. No. 13/522,717.
Official Action Dated Aug. 18, 2010 From the US Patent and Trademark Office Re. U.S. Appl. No. 12/083,436.
Official Action Dated Jul. 19, 2012 From the US Patent and Trademark Office Re. U.S. Appl. No. 12/083,436.
Official Action Dated Apr. 20, 2015 From the US Patent and Trademark Office Re. U.S. Appl. No. 13/497,055.
Official Action Dated May 20, 2011 From the US Patent and Trademark Office Re. U.S. Appl. No. 12/083,436.
Official Action Dated Dec. 21, 2012 From the US Patent and Trademark Office Re. U.S. Appl. No. 13/001,433.
Official Action Dated Sep. 26, 2014 From the US Patent and Trademark Office Re. U.S. Appl. No. 13/497,055.
Requisition by the Examiner Dated Feb. 7, 2015 From the Canadian Intellectual Property Office Re. Application No. 2,563,657.

(56) References Cited

OTHER PUBLICATIONS

Requisition by the Examiner Dated Mar. 19, 2013 From the Canadian Intellectual Property Office Re. Application No. 2,613,713.
Restriction Official Action Dated May 13, 2009 From the US Patent and Trademark Office Re. U.S. Appl. No. 11/587,179.
Restriction Official Action Dated Mar. 17, 2013 From the US Patent and Trademark Office Re. U.S. Appl. No. 13/522,717.
Restriction Official Action Dated Jan. 20, 2011 From the US Patent and Trademark Office Re. U.S. Appl. No. 12/306,934.
Restriction Official Action Dated Jan. 21, 2011 From the US Patent and Trademark Office Re. U.S. Appl. No. 12/306,933.
Restriction Official Action Dated Oct. 25, 2012 From the US Patent and Trademark Office Re. U.S. Appl. No. 13/001,433.
Statement of Opinion Dated Sep. 10, 2013 From the Korean Intellectual Property Office Re. Application No. 10-2008-7001219 and Its Translation Into English.
Supplementary European Search Report and the European Search Opinion Dated Sep. 16, 2011 From the European Patent Office Re. Application No. 09773059.2.
Supplementary Partial European Search Report and the European Search Opinion Dated Nov. 19, 2009 From the European Patent Office Re. Application No. 07766875.4.
Translation of Notice of Reasons for Rejection Dated Dec. 14, 2010 From the Japanese Patent Office Re. Application No. 2007-509059.
Translation of Office Action Dated Sep. 19, 2010 From the State Intellectual Property Office of the People's Republic of China Re. Application No. 200680032507.9.
Translation of Office Action Dated Jan. 21, 2013 From the State Intellectual Property Office of the People's Republic of China Re. Application No. 200680032507.9.
Translation of Rejection Decision Dated Aug. 31, 2012 From the State Intellectual Property Office of the People's Republic of China Re. Application No. 200680032507.9.
Official Action Dated Oct. 16, 2015 From the US Patent and Trademark Office Re. U.S. Appl. No. 13/522,717.
Supplementary European Search Report and the European Search Opinion Dated Jul. 18, 2011 From the European Patent Office Re. Application No. 09773060.0.
Supplementary Partial European Search Report and the European Search Opinion Dated Oct. 19, 2009 From the European Patent Office Re. Application No. 07766874.7.
Examination Report Dated Dec. 31, 2012 From the Government of India, Patent Office, Intellectual Property Building Re. Application No. 3402/KOLNP/2006.
Official Action Dated Jan. 25, 2016 From the US Patent and Trademark Office Re. U.S. Appl. No. 14/012,624.
Examination Report Under Sections 12 & 13 of the Patents Act, 1970 and the Patents Rules, 2003 Dated May 10, 2016 From the Government of India, Patent Office, Intellectual Property Building Re. Application No. 439/KOLNP/2008.
Supplementary European Search Report Dated Jul. 1, 2016 From the European Patent Office Re. Application No. 13861353.4.
International Search Report and the Written Opinion Dated Oct. 13, 2015 From the International Searching Authority Re. Application No. PCT/IL2015/050582.
Notice of Allowance Dated Jun. 7, 2013 From the US Patent and Trademark Office Re. U.S. Appl. No. 11/477,812.
Notice of Allowance Dated Jun. 25, 2010 From the US Patent and Trademark Office Re. U.S. Appl. No. 11/587,179.
Official Action Dated Jul. 6, 2012 From the US Patent and Trademark Office Re. U.S. Appl. No. 11/477,812.
Official Action Dated Feb. 23, 2011 From the US Patent and Trademark Office Re. U.S. Appl. No. 11/477,812.
Official Action Dated Nov. 28, 2011 From the US Patent and Trademark Office Re. U.S. Appl. No. 11/477,812.
Restriction Official Action Dated Sep. 13, 2010 From the US Patent and Trademark Office Re. U.S. Appl. No. 11/477,812.
Official Action Dated Nov. 10, 2016 From the US Patent Trademark Office Re. U.S. Appl. No. 13/522,717. (14 pages).
European Search Report issued for European Patent Application No. 06809092.7-1651 / 1948290, dated Nov. 8, 2013.
Official Action Dated Jul. 28, 2016 From the US Patent and Trademark Office Re. U.S. Appl. No. 13/522,717.
Restriction Official Action Dated Aug. 2, 2016 From the US Patent and Trademark Office Re. U.S. Appl. No. 13/520,345.
Communication Pursuant to Article 94(3) EPC Dated Feb. 3, 2017 From the European Patent Office Re. Application No. 13861353.4. (7 Pages).
Office Action and Search Report Dated Jan. 4, 2017 From the State Intellectual Property Office of the People's Republic of China Re. Application No. 201380071889.6 and Its Translation Into English. (12 Pages).
Notice of Reason for Rejection dated Aug. 8, 2017 From the Japan Patent Office Re. Application No. 2015-546149 and Its Machine Translation Into English. (9 pages).

* cited by examiner

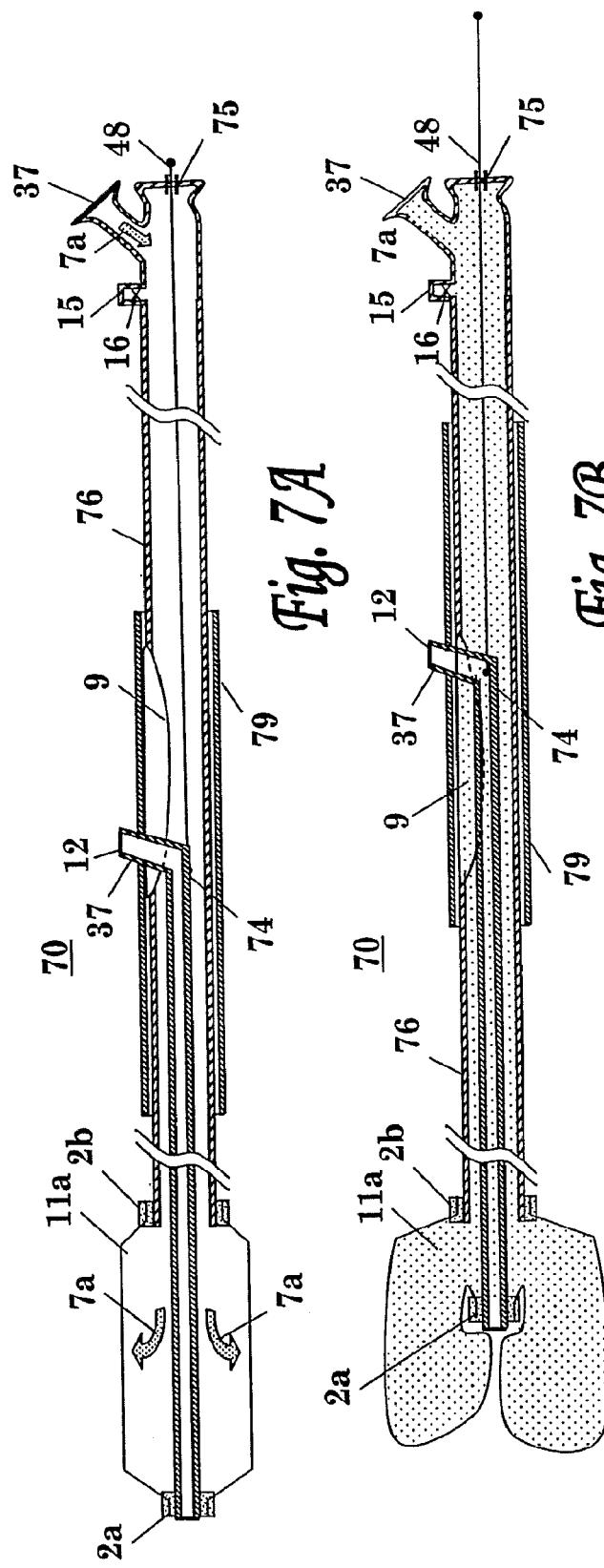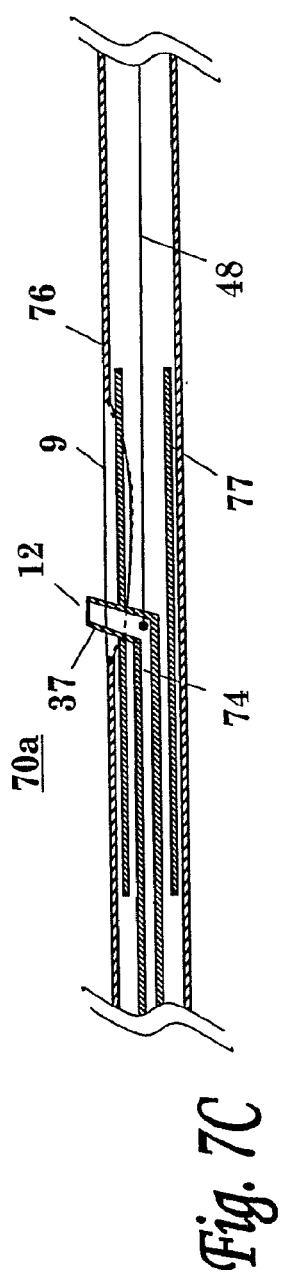

BALLOON CATHETER

This application is a continuation of U.S. Utility patent application Ser. No. 12/083,436, filed Mar. 13, 2009, which is the U.S. national phase of International Application No. PCT/IB2006/002955, filed 13 Oct. 2006, which designated the U.S., which is a continuation application of U.S. Utility patent application Ser. No. 11/477,812, filed 30 Jun. 2006, and claims priority to U.S. Provisional Patent Application No. 60/726,160, filed 14 Oct. 2005, and the entire contents of each of which are hereby incorporated by reference.

FIELD OF THE INVENTION

The present invention relates to balloon catheters. More particularly, the invention relates to a rapid exchange balloon catheter system, wherein the length and shape of the inflated balloon may be adjusted in situ.

BACKGROUND OF THE INVENTION

Rapid exchange ("monorail") catheters typically comprise a relatively short guide wire lumen provided at a distal end section thereof, and a proximal guide wire exit port located between the catheter's distal and proximal ends. This arrangement allows exchange of the catheter over a relatively short guide wire, in a manner which is simple to perform and which can be carried out by a single physician. Rapid exchange catheters have been extensively described in the art, for example, U.S. Pat. No. 4,762,129 (to Bonzel), U.S. Pat. No. 4,748,982 (to Horzewski) and EP0380873 (to Enger).

Rapid exchange catheters are commonly used in Percutaneous Transluminal Coronary Angioplasty (PTCA) procedures, in which obstructed blood vessels are typically dilated by a distal balloon mounted on the catheter's distal end. A stent is often placed at the vessel's dilation zone to prevent reoccurrences of obstruction therein. The dilation balloon is typically inflated via an inflation lumen which extends longitudinally inside the catheter's shaft between the dilation balloon and the catheter's proximal end.

The guide wire lumen passes within a smaller section of the catheter's shaft length and it is accessed via a lateral port situated on the catheter's shaft. This arrangement, wherein the inner tube is affixed to the catheter's shaft at the location of its lateral port, usually prevents designers from developing new rapid exchange catheter implementations which require manipulating the inner shaft. For example, extending or shortening the catheter's length during procedures may be advantageously exploited by physicians to distally extend the length of the catheter into a new site after or during its placement in the patient's artery, for example in order to assist with the passage of tortuous vessels or small diameter stenoses, or to allow in-situ manipulation of an inflated balloon at the distal end of the catheter.

The rapid exchange catheters of the prior art are therefore usually designed for carrying out a particular procedure and their implementations are relatively restricted as a consequence of the need for at least one catheter shaft to exit the catheter system laterally, between the proximal and distal ends of said system. Consequently, a need exists for a rapid exchange catheter that could overcome the above mentioned restriction and which would allow expansion of the range of applications of such catheters.

It is therefore an object of the present invention to provide a rapid exchange catheter having an adjustable balloon length and shape which may be modified during a procedure.

It is another object of the present invention to provide a rapid exchange balloon catheter wherein the shape and/or volume of a standard inflated balloon may be adjusted during a procedure.

It is a further object of the present invention to provide a rapid exchange balloon catheter capable of collecting samples and/or debris from the body treated site and reducing the risk of distal embolization of any material that may be dislodged during inflation of the balloon at the treated site.

Other objects and advantages of the invention will become apparent as the description proceeds.

SUMMARY OF THE INVENTION

The present invention provides rapid exchange (RX) catheter systems in which the length of a distal section of the catheter and the shape and/or volume of its distal balloon may be manipulated during procedures carried out therewith. Such implementations are ideally suited for use in debris collection applications, as will be described in detail hereinbelow. However, the RX configurations of the present invention may also be used in any other RX applications wherein it is necessary to alter the length of a distally-placed balloon element.

Consequently, the present invention is primarily directed to a rapid exchange catheter that permits axial movement of an inner conduit within an outer conduit comprising:
  a) an outer conduit;
  b) an inner conduit, suitable for total or partial passage over a guide wire, wherein said inner conduit is disposed within the lumen of said outer conduit such that the longitudinal axes of said inner and outer conduits are substantially parallel, wherein said inner conduit is capable of being moved along its longitudinal axis in relation to said outer conduit and wherein the proximal end of said inner conduit is angled such that it pierces the wall of said outer conduit;
  c) means for permitting said axial movement of said inner conduit within said outer conduit, such that said movement is not hindered by the passage of the angled proximal part of the inner conduit through said outer conduit; and
  d) means, situated at the proximal end of the outer conduit, for causing axial pushing-pulling movements of said inner conduit.

In one preferred embodiment of the above-defined rapid exchange catheter, the means for permitting unhindered axial movement of the inner conduit is provided by a sealing sleeve that is slidably fitted around the external conduit, such that the angled proximal portion of said inner conduit passes firstly through an elongated aperture in the wall of the external conduit, and secondly through a tightly sealed aperture in said sealing sleeve, such that upon axial movement of the inner conduit, said sealing sleeve is capable of preventing the transfer of fluid through said elongated aperture. The sealing sleeve is constructed such that it can provide a sealing effect under fluid pressure conditions appropriate for the balloon that is being inflated. Thus, in one non-limiting preferred embodiment, the sealing sleeve is capable of preventing fluid transfer through the elongated aperture at balloon inflation pressures of up to 16 atmospheres.

In another preferred embodiment, the above means for permitting unhindered axial movement of the inner conduit is provided by a two-part inner conduit construction, whereby the first, proximal part of said construction is non-movable, and wherein the second, distal part is slidably disposed within said proximal part.

In a further preferred embodiment, the abovementioned means for permitting unhindered axial movement of the inner conduit is provided by a two-part inner conduit construction, whereby the first, proximal part of said construction is non-movable, and wherein the second, distal part is slidably disposed over said proximal part.

In a still further preferred embodiment, the aforementioned means for permitting unhindered axial movement of the inner conduit is provided by a three-part inner conduit construction, whereby the first, proximal part of said construction is non-movable, and wherein the second, intermediate part is disposed within said proximal part, and wherein the third, distal part is slidably disposed within said intermediate part.

In another preferred embodiment of the rapid exchange catheter of the present invention, the means for causing axial movements of the inner conduit mentioned hereinabove comprise one or more wires, the distal end(s) thereof being attached to the inner conduit, and the proximal end(s) thereof extending beyond the proximal end of the outer conduit.

In another aspect, the present invention also provides a rapid exchange balloon catheter system comprising:
 a) an outer conduit;
 b) an inner conduit, suitable for total or partial passage over a guide wire, wherein said inner conduit is disposed within the lumen of said outer conduit such that the longitudinal axes of said inner and outer conduits are substantially parallel, wherein said inner conduit is capable of being moved along its longitudinal axis in relation to said outer conduit, wherein the proximal end of said inner conduit is angled such that it pierces the wall of said outer conduit, and wherein the distal tip of said inner conduit extends beyond the distal tip of said outer conduit;
 c) an angioplastic balloon whose proximal margin is attached to the outer surface of the distal tip of said outer conduit, and whose distal margin is attached to the outer surface of the portion of the inner conduit that extends beyond the distal tip of said outer conduit, and wherein the distal and/or proximal end portion(s) of said balloon are capable of intussusception upon proximal movement of said inner conduit in relation to said outer conduit;
 d) means, situated at the proximal end of the outer conduit, for causing axial pushing-pulling movements of said inner conduit;
 e) means for the introduction of an expansion fluid into the annular space formed between the inner surface of the outer conduit and the outer surface of the inner conduit and therefrom into the lumen of said balloon, and for the removal thereof;
 f) means for minimizing or preventing pressure changes within said annular space upon axial movement of said inner conduit in relation to said outer conduit; and
 g) means for permitting axial movement of said inner conduit within said outer conduit, such that said movement is not hindered by the passage of the angled proximal part of the inner conduit through said outer conduit.

In one preferred embodiment of the rapid exchange balloon catheter system defined hereinabove, said system is constructed such that the distal portion of the balloon is capable of intussusception upon proximal movement of the inner tube in relation to the outer tube.

In one preferred embodiment of this aspect of the invention, the means for causing axial movements of the inner conduit comprise one or more wires, the distal end(s) thereof being attached to the inner conduit, and the proximal end(s) thereof extending beyond the proximal end of the outer conduit.

In another preferred embodiment of this aspect of the invention, the means for preventing pressure changes comprises a plunger slidably disposed within the proximal end of the outer conduit, wherein said plunger is connected to the axial pushing-pulling means, such that upon operation of said pushing-pulling means, said plunger is caused to slide either distally or proximally, thereby changing the volume of the outer conduit.

Any suitable means may be employed for permitting unhindered axial movement of the inner conduit in the above-defined rapid exchange balloon catheter system. Preferably, however, these means are as defined in any one of the preferred embodiments disclosed hereinabove and claimed hereinafter.

In one preferred embodiment of the rapid exchange balloon catheter system of the present invention, the inner and outer conduits are characterized by their ability to withstand axially directed forces in the range of between 2 and 20 Newton without undergoing significant deformation. In the context of the present invention, the term "significant deformation" refers to changes in conduit length in excess of 5% of the total length of said conduit. While these conduits may be constructed of any suitable material capable of withstanding the aforementioned forces, in a preferred embodiment, the inner and outer conduits are constructed either from a biocompatible polymer (which in a preferred embodiment is selected from the group consisting of braided nylon thread and nylon thread that has undergone orientation treatment) or from flexible stainless steel tube. In one preferred embodiment of the rapid exchange balloon catheter system of the present invention, the balloon is, characterized by having, in its inflated state, a pre-folding profile, i.e. it has shape which is capable of assisting and guiding the intussusception of the distal portion thereof upon proximal movement of the inner conduit in relation to the outer conduit.

In one particularly preferred embodiment of the catheter system, the aforementioned balloon pre-folding profile is achieved by manufacturing the balloon such that it has (in its inflated state) a tapered shape with a rounded distal extremity.

Preferably, the balloon is constructed from Nylon 12, Pebax or mixtures thereof. It is to be recognized, however, that the balloon may also be constructed of any other suitable materials as are well known in the art, without deviating from the scope of the present invention as defined in the claims.

It should be noted that in each of the embodiments of the catheter, systems of the present invention disclosed and described hereinabove, a lubricant (such as silicone oil or mineral oil) may be present in order to facilitate the mutual sliding of the various conduits.

In another aspect, the present invention also provides a method for collecting debris from an internal passage of a mammalian subject comprising the steps of:
a) inserting a rapid exchange balloon catheter system as defined hereinabove into said internal passage, and advancing said catheter until the distal tip thereof has reached the site, at which it is desired to collect debris;
b) inflating the balloon with expansion fluid;

c) pulling the inner conduit of said balloon catheter in a proximal direction, such that the distal and/or proximal end(s) of said balloon intussuscept(s), d) deflating the balloon, thereby forming a cavity into which debris is collected and entrapped; and e) removing the balloon catheter from the internal passage of the subject, together with the entrapped debris.

In one preferred embodiment of the presently-disclosed method, the aforementioned internal passage is a vein or artery.

All the above and other characteristics and advantages of the present invention will be further understood from the following illustrative and non-limitative examples of preferred embodiments thereof.

BRIEF DESCRIPTION OF THE DRAWINGS

The present invention is illustrated by way of example in the accompanying drawings, in which similar references consistently indicate similar elements:

FIGS. 7A to 7C show longitudinal section views of a rapid exchange catheter according to a seventh preferred embodiment of the invention comprising a movable inner tube affixed to a slidable sealing sleeve;

DETAILED DESCRIPTION OF PREFERRED EMBODIMENTS

Figure 1A:
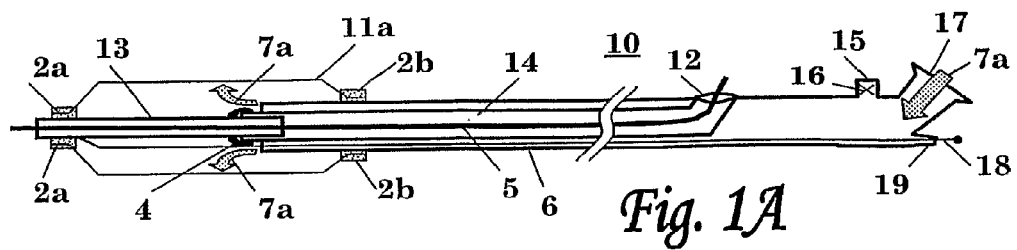
FIGS. 1A to 1C show longitudinal section views of a rapid exchange catheter according to one preferred embodiment of the invention wherein the distal section of the inner tube comprises an internal slidable tube.

The present invention aims to provide rapid exchange catheter implementations in which the length of a distal section of the catheter and the shape and/or volume of its distal balloon may be manipulated during procedures carried out therewith.

In general, the rapid exchange catheter of the invention comprises an outer catheter shaft and an inner tube provided therein, wherein the lumen of said inner tube may be accessed via a lateral port provided on the catheter's shaft. In some of the preferred embodiments of the present invention described herein the inner tube of the catheter is affixed to the catheter's outer shaft and the catheter's length and its balloon are manipulated by a unique construction of the inner tube. In these constructions the catheter's inner tube may comprise a slidable distal tube that may be moved by the operator, distally or proximally relative to the catheter's outer shaft, via a displacement rod attached thereto. Alternatively, the inner tube may be disposed within the lumen of a slidable intermediate tube which may be moved by the operator distally or proximally relative to the catheter's shaft.

In further embodiments of the invention a unique catheter construction is developed in order to provide a movable inner tube affixed to a slidable sealing sleeve which allows the operator to move the inner tube distally or proximally relative to the catheter's outer shaft and thereby manipulate its length and balloon.

FIG. 1 shows longitudinal section views of a first embodiment of the rapid exchange catheter 10 of the invention wherein the distal end of the catheter's inner tube 14 comprises a slidable internal tube 13. Catheter 10 comprises a hollow outer shaft 6 comprising inner tube 14 installed therein, and a slidable internal tube 13 placed in inner tube 14 such that it protrudes distally via a distal opening thereof. In this construction the inner lumens of inner tube 14 and slidable internal tube 13 are linked, thereby providing a continuous inner lumen ending at a distal opening of slidable internal tube 13. Proximal end of balloon 11a is attached to hollow outer shaft 6 at proximal attachment points 2b provided around the outer surface of a distal section thereof, and the distal end of said balloon is attached to the slidable internal tube 13 at distal attachment points 2a provided around the outer surface of a distal section of said slidable internal tube.

The lumen of inner tube 14 may be accessed via a lateral port 12 provided on hollow outer shaft 6, between the distal and proximal ends thereof. Guide wire 5 (or other suitable accessories) may be inserted via lateral port 12, advanced along the inner lumens of inner tube 14 and slidable internal tube 13, and exit the inner lumen of slidable internal tube 13 through a distal opening thereof.

Slidable concentric member 13 is adapted to fit into inner tube 14 and its diameter is preferably smaller than the diameter of inner tube 14 such that it seals its distal opening while comfortably permitting distal or proximal sliding of slidable internal tube 13 therethrough. Distal end portion of displacement rod 18 is attached to slidable internal tube 13 thereby allowing the operator to move slidable internal tube 13 distally or proximally relative to the catheter's outer shaft by pushing or pulling the proximal tip of displacement rod 18.

Further sealing of the distal opening of inner tube 14 may be achieved by an annular gasket 4 attached to the surface of distal tip of inner tube 14 such that a distal portion thereof is pressed against an annular portion of the outer surface of slidable internal tube 13.

The proximal portion of hollow shaft 6 comprises a fluid port 17 used for inflating or deflating balloon 11a by an inflation fluid pressurized therethrough, an optional discharge valve 16 installed in discharge valve outlet 15, and rod aperture 19 for moving displacement rod 18 distally or proximally therethrough.

During a typical procedure catheter 10 is inserted into a body treatment site in which balloon 11a may be inflated by an inflation fluid (designated by arrows 7a in FIG. 1A) pressurized through inflation fluid port 17, for effecting dilation or other procedures in said treatment site and/or for anchoring said balloon therein. The pressurized fluids pass via the hollow interior of hollow shaft 6 and reach the interior of balloon 11a via a distal opening of said shaft. In its inflated state, shown in FIG. 1B, the hollow interior of hollow shaft 6 and the internal space of balloon 11a are filled with pressurized inflation fluid. The distal opening of inner tube 14 is sealed by slidable internal tube 13 and (optionally) by gasket 4, thereby preventing leakage of pressurized inflation fluid thereinto. The pressure of the inflation fluid inside the system presses the gasket and improves the sealing provided by gasket 4. On the other hand, when the pressure of the inflation fluid is reduced the gasket's grip on the outer surface of inner tube 14 is diminished which makes it easier for the gasket to slide over it.

Figure 10:
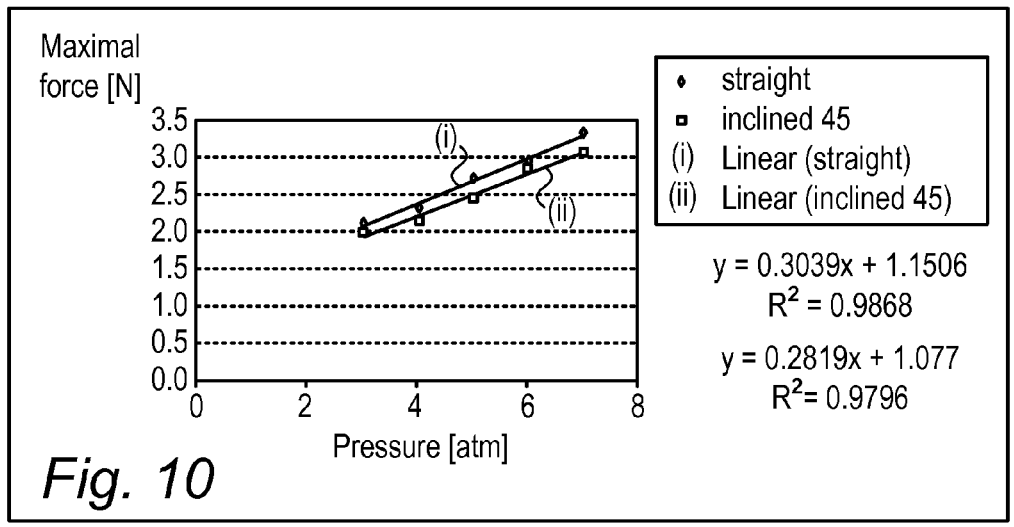
FIG. 10 graphically depicts the maximum force generated in the catheter tubes following balloon folding, measured for different balloon inflation pressures.

The requisite procedure is typically carried out in the inflated state of the balloon. By using the catheter of the invention for such procedures the operator may manipulate the catheter length and the shape and volume of balloon 11a by pulling displacement rod 18b, thereby moving slidable internal tube 13 proximally further into inner tube 14, as demonstrated by arrows 8a. As a result, the distal end of balloon 11a collapses and folds internally, as shown in FIG. 10, which increases the pressure of the inflation fluid. Whenever the pressure of the inflation fluid inside the hollow interior of hollow outer shaft 6 and in balloon 11a is above a predetermined threshold value a slender passage of discharge valve 16 is expanded to allow portions of inflation fluid to exit via discharge valve outlet 15 and thereby reduce the pressure of inflation fluid below said threshold value.

It should be noted that the use of pressure discharge elements and 16 constitutes merely one possible, exemplary means of pressure reduction.

Hollow outer shaft 6 is preferably made from a polymer or metal material, such as stainless 316, nitinol, or nylon, and it may be manufactured utilizing conventional methods, such as extrusion and laser cutting. The diameter of the hollow interior of hollow shaft 6 is generally in the range of 1-2 mm (millimeters), preferably about 1.2 mm, and the diameter of inflation fluid port 17 is generally in the range of 2-6 mm, preferably about 3 mm. The diameter of discharge valve outlet 15 is generally in the range of 2-6 mm, preferably about 3 mm, and the entire length of hollow shaft 6 is generally in the range of 500-2000 mm, preferably about 1200 mm.

Inner tube 14 is preferably made from a flexible polymer or metal material, such as pebax, nylon, stainless or nitinol and it may be manufactured utilizing conventional methods, such as extrusion and laser cutting. The diameter of inner lumen of inner tube 14 is generally in the range of 0.3-1 mm, preferably about 0.8 mm, and its entire length is generally in the range of 100-300 mm, preferably about 120 mm. Slidable internal tube 13 is preferably made from a flexible polymer or metal type of material, such as pebax, nylon, stainless or nitinol, and it may be manufactured utilizing conventional methods, such as pebax, nylon, stainless or nitinol. The diameter of inner lumen of slidable internal tube 13 is generally in the range of 0.3-1 mm, preferably about 0.5 mm, and its entire length is generally in the range of 30-150 mm, preferably about 70 mm.

In view of the axially-directed stretching and buckling forces exerted on the inner and outer tubes during elongation and shortening of the balloon, said tubes need to be constructed such that they are able to withstand axially-directed forces in the range of between 2 and 20 Newton without undergoing deformation. In order to achieve this aim, the conduits may be constructed of a braided material or of materials having a defined molecular orientation. The approximate maximum forces that the inner and outer tubes need to withstand (for two difference size ranges of balloon) are as follows:

2.5-4 mm balloons: the tubing should withstand up to 500 g; polymer tubing made of nylon or pebax reinforced during the manufacturing process can be used.

4-5 mm (or larger) balloons: the tubing should withstand forces up to 2 kg. In this case it will be necessary to use a braided tube (polymer tube with metal mesh reinforcement).

Results for a representative study of the forces generated during balloon folding are presented in Example 2, hereinbelow.

Balloon 11a is preferably a type of non-compliant or semi-compliant or low-compliant balloon such as manufactured by Interface Associates (USA). It may be manufactured utilizing conventional methods known in the balloon catheter industry from a biocompatible polymer type of material such as nylon 12 PET. Its length is generally in the range of 5-50 mm, preferably about 20 mm, and its diameter is generally in the range of 2 to 12 mm, preferably about 3 to 5 mm. The proximal and distal edges of balloon 11a are preferably adhered to the outer surfaces of hollow shaft 6 and slidable internal tube 13, at circumferential attachment points 2b and 2a respectively, by utilizing a low profile type of adhesion such as thermo bonding, UV adhesives or acrylic manufactured by Locktight. Preferably, the balloon should have a burst pressure within the range of 12-20 atmospheres.

The shape of balloon 11a has been found by the present inventors to be critical in order for said balloon to fulfill its intended functions in the presently-disclosed and claimed catheter system, namely:

i. to facilitate folding in such a way that the desired annular space is formed at the distal end of the intussuscepted balloon, by the application of the lowest possible retracting force;

ii. to create a cavity inside the balloon during and after deflation; and iii. to present a low profile that will facilitate introduction and withdrawal of the deflated balloon into and out of the catheter system and body passage.

The materials and design of the balloon, especially the shape of the distal taper and the relationship between the distal and the proximal taper, thus allow the balloon to fold smoothly and with relatively low pulling forces. This also insures that the balloon will fold only its distal side.

It appears, from modeling studies performed by the inventors, that a tapered balloon with a smooth round ending folds best and has a relatively low retracting force, when compared to standard tapered balloon or a balloon with a round ending. In a particularly preferred embodiment, the balloon has a proximal taper cone shaped with a 15-17 degree angle, and a 15 degree round cone distal taper, having a radius of about 0.5 mm at the junction of the taper and the neck. The results of the aforementioned modeling studies are presented in Example 1, hereinbelow.

Displacement rod 18 may be manufactured from a metal wire or tube, such as Stainless steel, Nitinol (Nickel Titanium) and/or from a polymer, having a diameter generally in the range of 0.2-2 mm, preferably about 0.5 mm, and length generally in the range of 50-150 mm, preferably about 100 mm. Distal portion of displacement rod 18 may be adhered to the distal section of slidable internal tube 13. Most preferably, distal portion of displacement rod 18 may be combined into the wall of internal tube 13 thereby enhancing its rigidity and the grip provided therewith. Rod aperture 19 is adapted to allow conveniently moving displacement rod 18 therethrough while providing suitable sealing of the hollow interior of hollow shaft 6, thereby preventing leakage of inflation fluid therefrom.

The inflation fluid is preferably a saline or a saline mixed with radio-opaque solution in different ratios. A syringe pump, or other suitable inflation pumps, as commonly used in the field, may be used for introducing the inflation fluid into the system. The pressure in the system in its various states is typically in the range of 0 to 25 atmospheres.

While different discharge valves may be employed, discharge valve 16 is preferably implemented by an annular element having an axial slender passage passing therein. In such implementation discharge valve 16 is manufactured from an elastomer type of material, such as PVC by an injection molding process. Its outer diameter is generally in the range of 2-6 mm, preferably about 4 mm, and its slender passage is designed to expand whenever a pressure gradient of about 4 bar evolves between its ends.

Figure 1B:
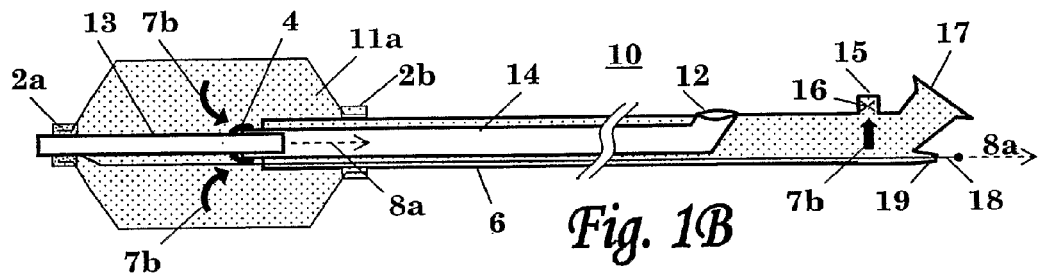
Figure 1C:
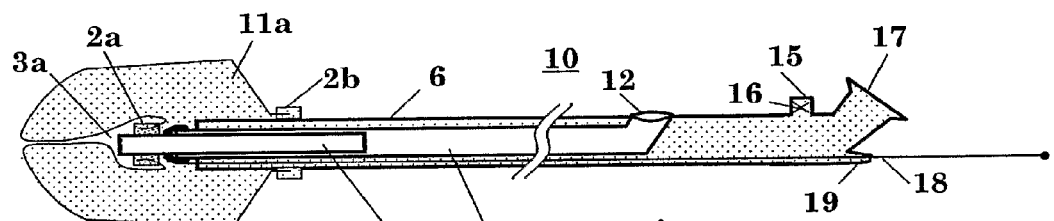
Figure 1D:
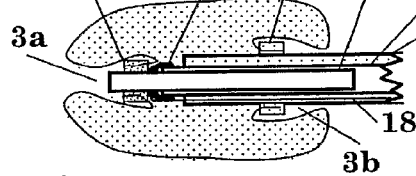
FIGS. 1D and 1E demonstrate the use of different balloons for different manipulations thereof.
Figure 1F:
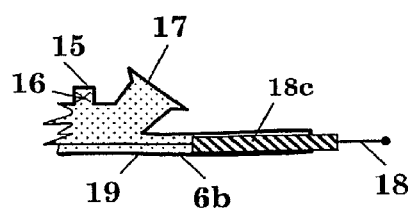
FIG. 1F demonstrates a piston-like construction for preventing pressure accumulation within the catheter during retraction.

Optionally, a proximal part 18c of rod 18 is made to be wide enough to occupy a volume of space within a proximal portion 6b of hollow shaft 6, as shown in FIG. 1F. This piston-like construction 18c allows for a syringe like action of rod 18 when retracted proximally, causing it to evacuate enough space in the proximal potion 6b of the lumen of hollow shaft 6. This extra space will then be filled by inflation fluid, thereby preventing pressure accumulation within the catheter during retraction of the rod 18.

As shown in FIG. 10 in its folded state distal cavity 3a is obtained by the inwardly folded distal sections of balloon 11a. The volume encompassed by cavity 3a may be enlarged by (partially or entirely) deflating the balloon in this folded state, thereby filling the enlarged cavity with samples and/or debris from the treatment site. Different distal balloons may be designed to provide various balloon manipulations as exemplified in FIGS. 1D and 1E.

Figure 1E:
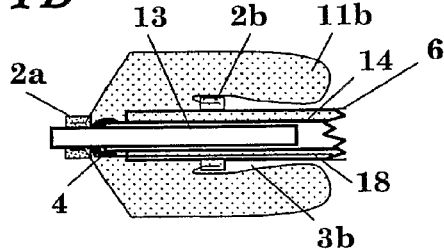

For example, in balloon 11b shown in FIG. 1E a proximal section of the balloon collapses and folds inwardly in response to movement of slidable internal tube 13 proximally, thereby forming a proximal cavity 3b. Such a result may be achieved by using a balloon which has higher resistance to folding at its proximal tapered end relative to its distal tapered end This can be achieved by using a balloon having different angles at its distal and proximal tapers, wherein a steeper taper facilitates its folding.

As another example, in balloon 11ab shown in FIG. 1D both, proximal and distal, sections of the balloon are folded in response to movement of slidable internal tube 13 proximally, thereby forming a proximal cavity 3b and a distal cavity 3a. This result may be obtained for example by using a balloon 11ab with a symmetric shape—namely, the balloon having the same taper at its distal and proximal sides.

The procedure for using the balloon catheter of the present invention may be briefly described as follows:

1) Insertion of catheter into the body via peripheral blood vessel by use of standard rapid exchange methods, as are well known in the art;
2) Inflation of the balloon by injecting inflation fluids via fluid port 17 and the inner lumen of outer shaft 6, as demonstrated by fluid inflation arrows 7a in FIG. 1A; the pressure inside balloon 11 may be in general about 1-25 Atmospheres, preferably about 6 Atmospheres.
3) In this state, with the balloon catheter 10 firmly anchored at the treatment site, the inner lumens of inner tube 14 and of slidable internal tube 13 may now be utilized for operating at the treated site with different interventional tools (not shown), as may be required.
4) If required, a sample or other liquid or solid matter (for example fluids, secretions, and/or debris) may be collected from the treatment site, by pulling proximally displacement rod 18 thereby releasing retracting slidable internal tube 13 proximally, as demonstrated by arrow 8a in FIG. 1B. During retraction of slidable internal tube 13 by the operator the distal tip of balloon 11 collapses and its outer surface portions are folded inwardly over the distal tip of slidable internal tube 13 and thereafter over itself as further portions of the balloon collapse, as illustrated in FIG. 1C.
5) Retraction of slidable internal tube 13 and the resulting inward folding of balloon 11 shorten the overall length of inflated balloon 11 which actually reduces the volume of inflated balloon 11. Consequently, the pressure exerted by the inflating fluids increases, resulting in a considerable pressure increase in balloon 11 and inner lumen of outer shaft 6. Whenever the pressure in balloon 11 and inner lumen of outer shaft 6 reaches a certain set-point (e.g., 5-20 atmospheres) inflation fluids can be discharged via discharge valve 16, as shown by arrows 7b in FIG. 1B, such that the pressure in balloon 11 and inner lumen of outer shaft 6 remains within a predetermined pressure range (e.g., 5-20 atmospheres). Another exemplary option for discharging pressure is by widening the proximal section 18c of rod 18 so it can act similar to a syringe action, as shown in FIG. 1F. During this step the operator can determine via a graduated scale (not shown) provided on rod 18 the amount of length of inner tube 14 that has been retracted and in this way determine when to stop the retraction of inner tube 14.
6) Subsequently, balloon 11 is deflated by retracting inflation fluids via fluid port 17. As a result, the pressure inside balloon 11 and inner lumen of outer tube 6 is substantially decreased, and balloon 11 is deflated. The reduction in the volume of balloon 11 results in enlargement of distal cavity 3a.

The operator then retracts balloon catheter 10 proximally such that portion of fluid/secretion and debris confined within proximal cavity 3a are withdrawn with the balloon catheter 10 (not shown in the figures). The debris, objects or samples collected may be easily collected when the entire length of balloon catheter 10 is ejected from the body of the treated subject, by pushing the inner tube 14 distally and unfolding the folded portions of balloon 11, thus restoring the deflated state of balloon 11 (shown in FIG. 1A).

Figure 2A:
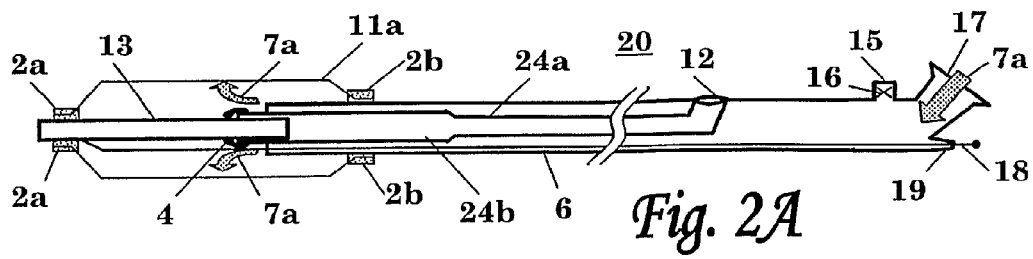
FIGS. 2A to 2C show longitudinal section views of a rapid exchange catheter according to a second preferred embodiment of the invention wherein the diameter of the distal section of the inner tube is adapted to receive an internal slidable tube.
Figure 2B:
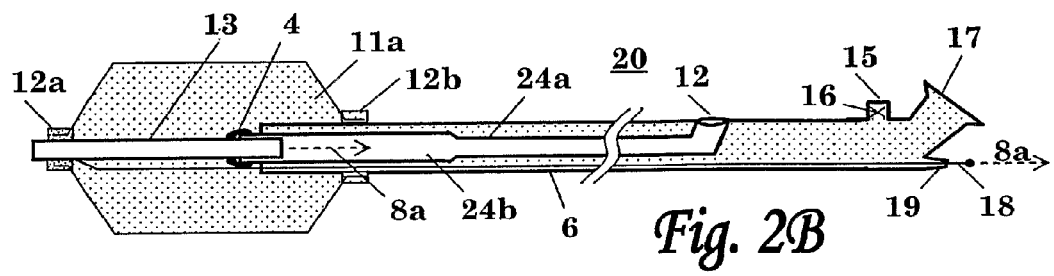
Figure 2C:
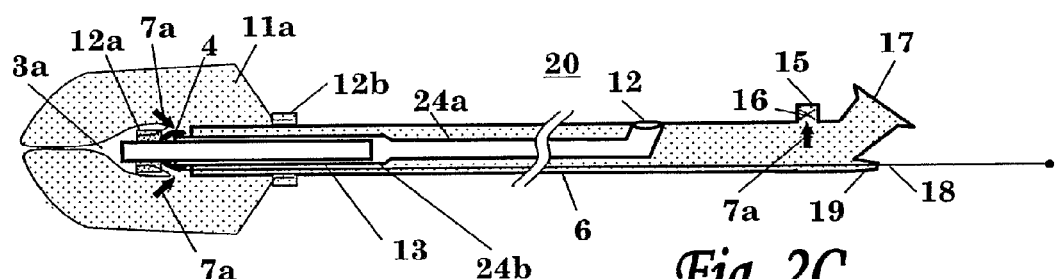

FIGS. 2A to 2C show longitudinal section views of a rapid exchange catheter 20 according to a second preferred embodiment of the invention wherein the diameter of a distal section 24b of the inner tube 24a is adapted to receive internal slidable tube 13. In this preferred embodiment the diameter of distal section 24b of inner tube 24a is made relatively greater than the diameter of the proximal section thereof. Internal slidable tube is designed to tightly fit into proximal section 24b and thereby seal its distal opening and prevent leakage of inflation fluid thereinto. Alternatively or additionally, sealing may be achieved by gasket 4 attached to the distal section 24b of inner tube 24a such that a distal portion thereof is pressed against an annular portion of the outer surface of slidable internal tube 13. Internal slidable tube 13 and the proximal section of inner tube 24m may be manufactured to have the same inner diameter, thereby forming a substantially homogenous inner lumen therebetween, particularly when internal slidable tube 13 is advanced all the way into distal section 24b.

The structure and geometrical dimensions of elements of catheter 20 are much the same as those elements designated by the same numerals which were described above with reference to FIGS. 1A to 1C. In addition, the construction of the catheter tubes such that they are able to withstand the axially-directed stretching and buckling forces in this, and in all subsequent embodiments, are as described hereinabove, in connection with the first-described embodiment. Similarly, balloon 11a may be inflated by inflation fluid (7a) pressurized via inflation fluid port 17, and catheter's 20 length and the shape and volume of balloon 11a may be manipulated by moving displacement rod 18 distally or proximally, as exemplified in FIGS. 2A to 2C. Different balloons may be designed to provide various balloon folding configurations as exemplified in FIGS. 1D and 1E. The optimal balloon shape for use with this, and with all subsequently described embodiments is as described hereinabove, with reference to the first described embodiment.

Inner tube 24a may be manufactured by an extrusion and laser cutting process from a plastomeric or metallic type of material, preferably from nylon, PET or stainless steel. The diameter of the distal section of inner tube 24a is generally in the range of 0.3-2 mm, preferably about 0.5 mm, and the diameter of slidable internal tube 13 is adapted to provide tight fitting and the necessary sealing of distal opening of inner tube 24a when said internal tube is inserted thereinside.

Figure 3:
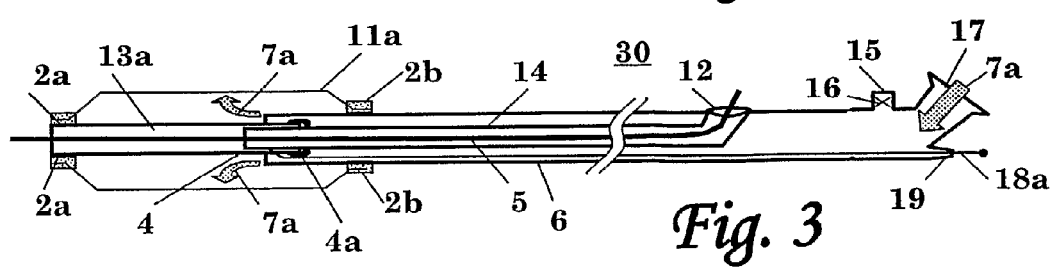
FIG. 3 shows a longitudinal section view of a rapid exchange catheter according to a third preferred embodiment of the invention wherein the distal section of the inner tube comprises an external slidable tube.

FIG. 3 shows a longitudinal section view of catheter 30 according to a third preferred embodiment of the invention wherein the distal section of the inner tube 14 comprises an external slidable tube 13a. In this preferred embodiment the distal end of balloon 11a is attached to the slidable external tube 13a at distal attachment points 2a provided around the outer surface of a distal section of said slidable external tube. The diameter of external slidable tube 13a is made relatively greater than the diameter of inner tube 14. External slidable tube 13a is designed to tightly fit over the outer surface of the proximal section of inner tube 14 and to thereby seal its distal opening and prevent leakage of inflation fluid thereinto. Alternatively or additionally, sealing may be achieved by gasket 4 attached to the proximal end portion of external slidable tube 13a such that a proximal portion thereof is pressed against an annular portion of the outer surface of inner tube 14.

Using such external slidable tube 13a in catheter 30 permits the attachment of a relatively short displacement rod 18a to the proximal section of said slidable tube 13a. Alternatively or additionally, the distal portion of displacement rod 18a may be combined into the wall of external slidable tube 13a along its longitudinal length, thereby enhancing its rigidity and the grip provided therewith.

The structure, geometrical dimensions of elements of catheter 30 designated by the same numerals, and the method of manipulating its length and balloon volume and shape, are much the same as those elements and manipulating method which were previously described hereinabove and therefore, for the sake of brevity, said elements will not be further discussed at this point. External slidable tube 13a may be manufactured by an extrusion and laser cutting process from a plastomeric or metallic type of material, preferably from nylon or stainless steel. The diameter of external slidable tube 13a is adapted to provide tight fitting and the necessary sealing of distal opening of inner tube 14 when said external slidable tube is mounted thereover. For example, the diameter of external slidable tube 13a may be in the range of 0.3-2 mm, preferably about 0.8 mm.

Figure 4:
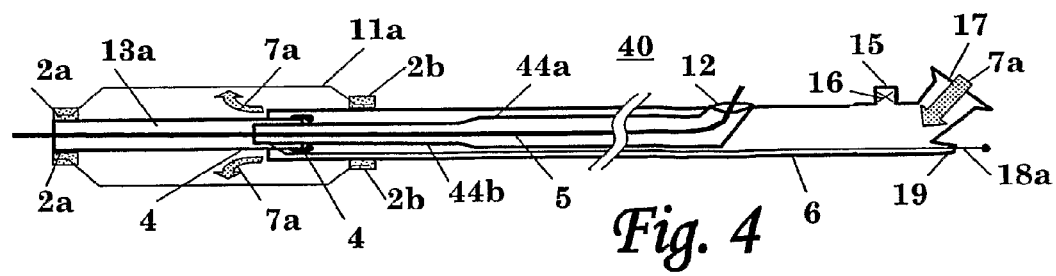
FIG. 4 shows a longitudinal section view of a rapid exchange catheter according to a fourth preferred embodiment of the invention wherein the diameter of the distal section of the inner tube is adapted to be received in an external slidable tube.

A fourth preferred embodiment (40) of the invention is demonstrated in the longitudinal section view shown in FIG. 4, wherein the diameter of the distal section 44b of inner tube 44a is adapted to be received in an external slidable tube 13a. In this preferred embodiment the distal end of balloon 11a is attached to the slidable external tube 13a at distal attachment points 2a provided around the outer surface of a distal section of said slidable external tube. The diameter of distal section 44b of inner tube 44a is made relatively smaller than the diameter of the proximal section thereof. External slidable tube 13a is designed to tightly fit over proximal section 44b and thereby seal its distal opening and prevent leakage of inflation fluid thereinto. Alternatively or additionally, sealing may be achieved by gasket 4 attached to the proximal end of External slidable tube 13a such that a proximal portion thereof is pressed against an annular portion of the distal section 44b of inner tube 44a.

The external slidable tube 13a of catheter 40 allows attachment of a relatively short displacement rod 18a to the proximal section of said slidable tube 13a. Alternatively or additionally, the distal portion of displacement rod 18a may be combined into the wall of external slidable tube 13a along its longitudinal length, thereby enhancing its rigidity and the grip provided therewith.

The structure, geometrical dimensions of elements of catheter 40 designated by the same numerals, and the method of manipulating its length and balloon's volume and shape, are much the same as those elements and the manipulating method which were previously described hereinabove and therefore will not be further discussed here. Inner tube 44a may be manufactured by an extrusion and laser cutting process from a plastomeric or metallic type of material, preferably from nylon or stainless steel. The diameter of the distal section 44b of inner tube 44a is generally in the range of 0.3-2 mm, preferably about 0.5 mm, and the diameter of external slidable tube 13a is adapted to provide tight fitting and the necessary sealing of distal opening of inner tube 44a when said external tube is mounted thereover.

Figure 5:
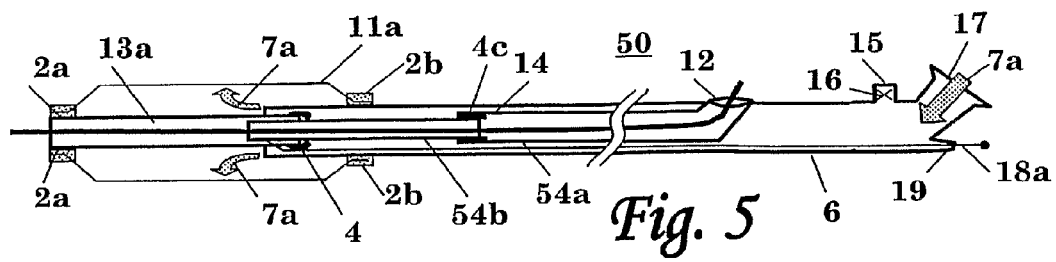
FIG. 5 shows a longitudinal section view of a rapid exchange catheter according to a fifth preferred embodiment of the invention wherein the distal section of the inner tube comprises a fixed inner tube (on which an external slidable tube is mounted.

In a fifth preferred embodiment of the invention, illustrated in the longitudinal section view shown in FIG. 5, an external slidable tube 13a is mounted over an inner tube 54b protruding distally through a distal opening of fixed inner tube 54a of catheter 50. In this preferred embodiment the distal end of balloon 11a is attached to the slidable external tube 13a at distal attachment points 2a provided around the outer surface of a distal section of said slidable external tube. A proximal end portion of inner tube 54b is fitted into a distal opening of fixed inner tube 54a, such that it seals said distal opening and most of its longitudinal length protrudes distally therefrom into the hollow interior of hollow shaft 6. The diameter of external slidable tube 13*a* is adapted to tightly fit over the external surface of inner tube 54*b*, thereby sealing its distal opening while allowing it to be easily moved distally or proximally thereon by the operator.

Sealant 4*c* may be applied to the proximal end of inner tube 54*b* in order to provide enhanced sealing of the distal opening of fixed inner tube 54*a*. Sealing of the distal opening of inner tube 54*b* may be achieved by an annular gasket 4 attached to the proximal tip of external slidable tube 13*a* such that a proximal portion thereof is pressed against an annular portion of the outer surface of inner tube 54*b*.

Gaskets 4 can be made of a flexible material such as silicone or polyurethane. Alternatively, gaskets 4 may be implemented by an added lubricant such as mineral oil or silicone oil which improves the sliding between the tubes. The sealing may be further increased by increasing the pressure in the balloon.

It should be noted that tubes 13*a* and 54*a* may be fixed tubes such that tube 54*a* is fixed to the shaft 6 and tube 13*a* is fixed to the distal neck of balloon 11*a*, such that tube 54*b* can slide into both tubes.

The structure, geometrical dimensions of elements of catheter 50 designated by the same numerals, and the method of manipulating of its length and balloon's volume and shape, are much the same to those elements and manipulating method which were previously described hereinabove and therefore will not be discussed here, for the sake of brevity. Fixed inner tube 54*a* and external slidable tube 13*a* may be manufactured by an extrusion and laser cutting process from a plastomeric or metallic type of material, preferably from nylon or flexible metal. Their diameters are adapted to provide tight fitting and the necessary sealing of distal openings of fixed inner tube 54*a* and of inner tube 54*b*.

Figure 6A:
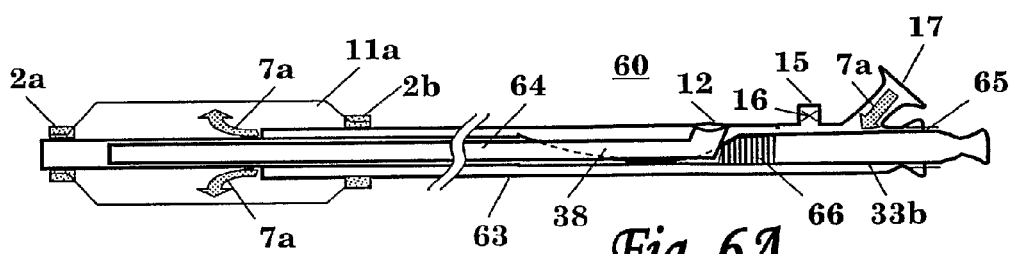
FIGS. 6A to 6C show longitudinal section views of a rapid exchange catheter according to a sixth preferred embodiment of the invention wherein the inner tube of the catheter is encompassed by a slidable intermediate tube.
Figure 6B:
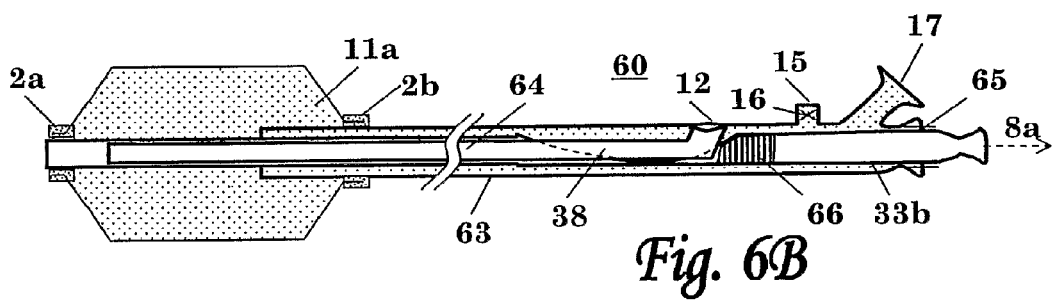
Figure 6C:
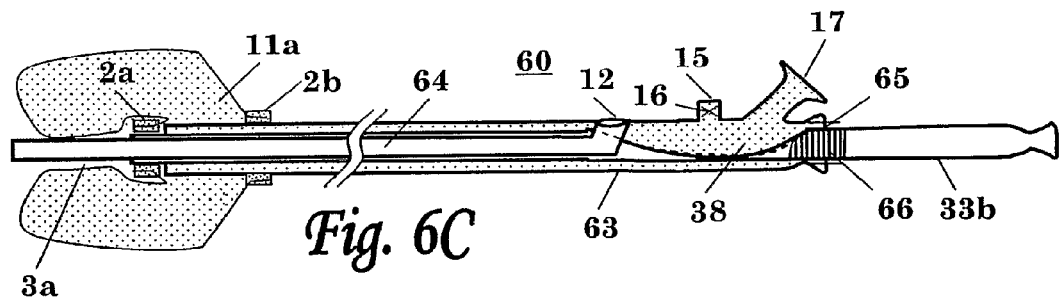

FIGS. 6A to 6C show longitudinal, section views of a sixth preferred embodiment of the invention in which the inner tube 64 of catheter 60 is encompassed in a slidable intermediate tube 33*b*. In this preferred embodiment the distal end of balloon 11*a* is attached to the slidable intermediate tube 33*b* at distal attachment points 2*a* provided around the outer surface of a distal section of said slidable intermediate tube. Horizontal opening 38 is provided on an upper side of slidable intermediate tube 33*b*. Inner tube 64 protrudes upwardly through horizontal opening 38 towards the upper side of hollow shaft 6 at the location in which it is affixed thereto and provide an access to its lumen via lateral port 12.

During a procedure balloon 11*a* may be inflated by pressurized fluid (designated by arrows 7*a* in FIG. 6A) provided via inflation fluid port 17. As illustrated in FIG. 6B, pressurized fluid passes through the hollow interior of hollow shaft 63 into the internal space of balloon 11*a*. The catheter and its balloon in the inflated state are illustrated in FIG. 6B. The proximal section of intermediate tube 33*b* between horizontal opening 38 and the proximal end of intermediate tube 33*b* may be sealed by a sealant 66 in order to prevent entry of inflation fluids thereinto. Whenever the pressure in balloon 11*a* and hollow interior of hollow shaft 63 is greater than a predetermined threshold value, a portion of the inflation fluids is discharged via discharge valve 16 installed in discharge valve outlet 15.

The proximal section of intermediate tube 33*b* protrudes proximally via proximal opening 65 provided at the proximal end of shaft 63. Proximal opening 65 is designed to conveniently allow the sliding of intermediate tube 33*b* therethrough while providing suitable sealing thereof and preventing leakage of inflation fluid therefrom. Manipulation of the catheter length and its balloon shape and volume are performed by sliding the intermediate tube 33*b* proximally or distally relative to the catheter shaft.

For example, after inflating balloon 11*a* the operator may pull the proximal section of intermediate tube 33*b* (shown by arrow 8*a* in FIG. 6B) thereby causing distal section of balloon 11*a* to collapse and fold inwardly and deform cavity 3*a*, as illustrated in FIG. 6C. Horizontal opening 38 is adjusted to allow sliding intermediate tube 33*b* proximally into a state in which attachment point 2*a* reaches the distal end of shaft 63, and on the other hand, to allow sufficient distal sliding of intermediate tube 33*b* in order to enable stretching the full length of balloon 11*a*.

Intermediate tube 33*b* may be manufactured by extrusion or laser cutting processes, from a plastomer or metallic type of material such as nylon, Teflon, or flexible stainless steel. The diameters of inner tube 64 and of intermediate tube 33*b* are adapted to allow insertion of inner tube into the lumen of intermediate tube 33*b* while providing suitable sealing thereof and preventing leakage of inflation fluids thereinto. For example intermediate tube 33*b* may have an inner diameter of about 0.8 mm and the outer diameter of inner tube 64 may be of about 0.78 mm.

Intermediate tube 33*b* can be manufactured by an extrusion process in which the ID (internal diameter) has an appropriate tolerance to fit over the outer diameter of inner tube 64. Inner tube 64 and intermediate tube 33*b* are assembled together such that lateral port 12 is located in the horizontal opening 38 of intermediate tube 33*b*. Thereafter the tubes 64 and 33*b* are inserted into the hollow shaft 63 and lateral port 12 can be attached to hollow shaft 63.

It should be noted that intermediate tube 33*b* is not necessarily a complete tube. While the distal portion of intermediate tube 33*b* should be of a tubular shape, its proximal portion may have other cross-sectional shapes such as a semilunar shape. Alternatively, the proximal portion of intermediate tube 33*b* may be implemented by a wire attached to its distal portion and exiting catheter 60 via proximal opening 65.

FIGS. 7A to 7C show longitudinal section views of a catheter 70 according to a seventh preferred embodiment of the invention wherein the inner tube 74 is made movable by affixing it to a slidable sealing sleeve 79. In this preferred embodiment the distal end of balloon 11*a* is attached to the inner tube 74 at distal attachment points 2*a* provided around the outer surface of a distal section of said inner tube.

The structure, geometrical dimensions of elements of catheter 70 designated by the same numerals, and the method of manipulating its length and balloon's volume and shape, are much the same as those elements and manipulating method which were previously described hereinabove and therefore will not be further discussed herein, for the sake of brevity.

As with previous embodiments of the invention the inner tube 74 is disposed in the hollow interior of the catheter's hollow outer shaft 76 and a curved section 37 thereof comprising lateral port 12 protrudes outwardly therefrom. A lateral opening 9 is provided on hollow outer shaft 76 from which said curved section 37 of inner tube 74 is protruding outwardly from hollow shaft 76. Lateral opening 9 is sealed by sealing sleeve 79 mounted over an outer surface of hollow outer shaft 76. Sealing sleeve 79 is designed to tightly fit over the outer surface of hollow outer shaft 76, and to seal lateral opening 9 and the attachment area between sealing sleeve 79 and the curved section of inner tube 74 protruding therefrom. Moreover, sealing sleeve is also made slidable to allow its movement distally or proximally within the limits imposed by lateral opening 9.

In this way a movable inner tube 74 is obtained. The operator may inflate (designated by arrows 7a in FIG. 7A) balloon 11a and move inner tube distally or proximally by sliding sealing sleeve over hollow shaft 76. Additionally or alternatively, a displacement rod 48 may be employed for this purpose. Displacement rod 48 may be attached to a proximal section of inner tube 74 and a proximal section thereof can be made available to the operator via a proximal opening 75 provided at the proximal end of hollow shaft 76. Proximal opening 75 is designed to allow conveniently sliding displacement rod 48, therethrough while providing suitable sealing thereof and preventing leakage of inflation fluid therefrom.

Lateral opening 9 is adjusted to allow moving inner tube 74 proximally into a state in which attachment point 2a reaches the distal end of hollow shaft 76, and on the other hand, to allow sufficient distal movement of inner tube 74 in order to enable stretching of balloon 11a to its fullest length.

Sealing sleeve 79 can be manufactured by an extrusion and laser cutting process from a plastomer or metallic type of material, preferably from nylon or flexible stainless steel. The sealing and attachment of sealing sleeve 79 and the curved section 37 of inner tube 74 is preferably obtained by bonding these parts together by thermo-bonding or any other adhesive method such that they can slide together. The diameter of sealing sleeve 79 is adjusted according to the geometrical dimensions of hollow shaft 76. For example, if the diameter of hollow shaft is about OD (outer diameter) 1.2 mm then the diameter of sealing sleeve is made about ID 1.22 mm.

FIG. 7C demonstrates an implementation of catheter 70a, similar to catheter 70, wherein an inner sealing sleeve 77 is adapted to be installed in the hollow interior of hollow shaft 76. In this implementation inner sealing sleeve 77 is adapted to be pressed against the inner wall of hollow shaft 76 about the area of lateral opening 9 and thereby to provide suitable sealing thereof. As in catheter 70 illustrated in FIG. 7A, an essentially vertical section of inner tube 74 protrudes outwardly via inner sealing sleeve 77 and may be accessed by the operator via lateral port 12. The sealing and attachment of inner sealing sleeve 77 and vertical section of inner tube 74 may be obtained using the same means described above with reference to catheter 70.

Inner sealing sleeve 77 can be manufactured by an extrusion and laser cutting process from a plastomeric or metallic type of material, preferably from nylon or flexible stainless steel. The sealing and attachment of inner sealing sleeve 77 and the vertical section of inner tube 74 is preferably obtained in a similar manner as was explained hereinabove. The diameter of sealing sleeve 77 is adjusted according to the geometrical dimensions of hollow shaft 76. For example, if the diameter of hollow shaft is about ID 1 mm then the diameter of inner sealing sleeve is made about OD 0.98 mm.

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different tubes, balloons, shafts, and other members, described hereinabove may be constructed in different shapes (e.g. having oval, square etc. form in plan view) and sizes from those exemplified in the preceding description.

It should be noted that the different balloon catheter embodiments of the invention which were described hereinabove may be implemented with different types of balloon enabling folding of the proximal section of the balloon, the distal section of the balloon, or both proximal and distal sections of the balloon, as was exemplified hereinabove with reference to FIGS. 1D and 1E.

Furthermore, it should be noted that the different balloon catheter embodiments of the invention which were described hereinabove may be used for delivering a stent mounted on the balloon, and placing said stent in the treatment site as commonly performed in standard stent procedures.

EXAMPLES

Example 1

Finite Element Analysis (FEA) of a Debris-Collecting Balloon for Use in the Present Invention FEA is a computerized tool which was used to optimize the balloon design in order to improve its ability to fold in the desired way. The FE model describes an inflated balloon which edge is retracted, resulting in folding of the balloon. The simulation was performed on different balloon designs and at varied inflation pressures, taking into account the mechanical properties of the balloon material, which was chosen to be nylon 12 or pebax.

Assumptions:

i. The balloon is made of a homogenous and isotropic material.

ii. The balloon's shape is symmetrical around its longitudinal axis.

iii. The balloon's shape is symmetrical around its mid transverse axis.

iv. The folding results in flexural stresses in the balloon material. Thus the mechanical properties (Modulus and Poisson Ratio) of the substance when flexed are taken into account in the FE analyses.

Figure 8:
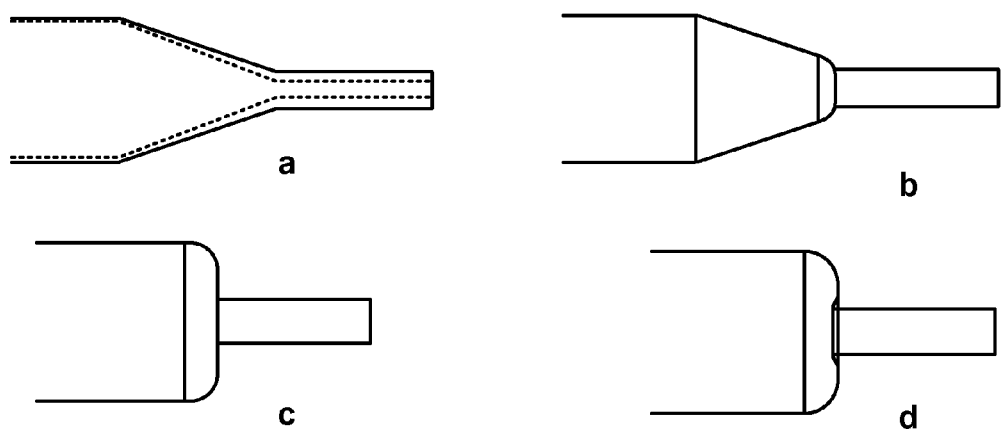
FIG. 8 schematically illustrates the four balloon designs that were analyzed and compared in the finite element analysis study: a. Standard 20° tapering; b. 20° tapering with smooth round ending; c. Round ending; d. Round ending with initial retracting.

Methods:

a) The analyses were performed using a nonlinear Finite Elements Analysis (FEA) program MSC.MARC. This software allows assessment of the structural integrity and performance of parts undergoing large deformations as a result of thermal or structural load (www.mscsoftware.com).

b) The analyses were nonlinear, assuming large displacements and taking into account stiffness change due to geometry update and sequential forces.

c) The model was 2D axisymmetric.

d) The model consisted of about 1000 nodes and 1000 2D solid elements.

e) Constant pressure was applied from within the balloon on its walls, reflecting the inflation pressure. Simultaneously, gradually increased axial force was exerted to the edge of the balloon, resulting in its folding. The displacement of the balloon wall in the horizontal (longitudinal) axis was measured versus the applied force.

f) The longitudinal axis of the balloon was kept fixed, while the balloon walls were free to move/fold as a result of the axial load.

g) The balloon's specifications are listed in the following table:

| Balloon Specifications | |
| --- | --- |
| Balloon length [mm] | 20 |
| Balloon Outer Diameter [mm] | 3 |
| Tube Outer Diameter [mm] | 0.4 |
| Balloon Body Wall Thickness [μm] | 10 |
| Neck Wall Thickness [μm] | 50 |
| Tube Wall Thickness [μm] | 100 |
| Tapering | varying |
| Material | PET (Polyethylene Terephthalate) |
| Mechanical Properties | |
| Flexural Modulus [Kg/mm$^2$] | 100 |
| Flexural Yield Strength [Kg/mm$^2$] | 8.15 |
| Poisson Ratio | 0.4 | h) Four balloon designs were analyzed, wherein the differences reside in the design of their tapering (see FIG. 8):

Standard 20° tapering

20° tapering with smooth round ending

Round ending

Round ending with initial retracting i) The simulations were performed at five different inflation pressures: 1, 3, 6, 9 and 12 atmospheres.

Figure 9:
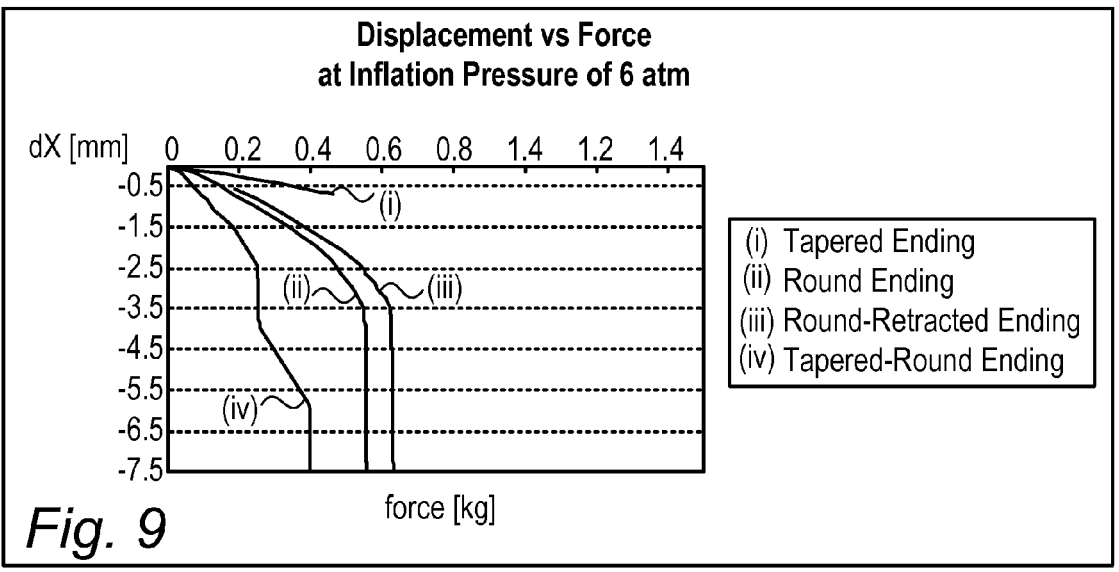
FIG. 9 graphically depicts the displacement vs. retracting force for the four balloon shapes, compared at an inflation pressure of 6 atmospheres.

Results:

FIG. 9 shows the displacement vs. retracting force for the four balloon shapes at an inflation pressure of 6 atmospheres. Considering the maximal force required for collapse of the balloon, the Tapered-Round Ending Balloon required the lowest force, whereas the Round Ending Balloons need the greatest force to collapse. The Tapered Ending Balloon is somewhere between them. The slope of the Tapered Ending Balloon in the initial phase seems to be relatively moderate compared to the other balloon configurations. The moderate slope indicates higher stiffness. In other words, higher force is required to induce a given displacement. The slope of the Tapered-Round Ending Balloon is the steepest one, and suggests relatively high compliance to folding.

The balloon retracted shape vs. the original shape, at different inflation pressures was also studied (results not shown). The results demonstrated that the Tapered Ending Balloon is barely retracted, compared to the Round Ending Balloons which are retracted in a more smooth and continuous fashion. This is in spite of the higher force required to fold them.

Conclusion:

From the above analyses it was concluded that the inflation pressure and the balloon geometry have an important role in determining of the required folding force and the folding style. It appears that a tapered balloon with a smooth round ending folds best and has a relatively low retracting force, when compared to standard tapered balloon or a balloon with a round ending.

Example 2

Determination of the Force that is Required in Order to Fold the Balloon at Different Inflation Pressure Equipment and Materials:

3.0 mm Nylon 12 Vestamid L2101F Balloon (Interface Associates 316079-1)

Glass tube with inner diameter of 3 mm.

Guidant HI-TORQUE CROSS-IT 200XT 0.014" Guidewire.

Hounsfield Test Equipment Model TX0927, 50-N load cell. This computer controlled testing machine enables determining tension, compression, shear, flexure and other mechanical and physical properties of materials. The machine provides selection of test speeds and direction of travel. It can measure the force and displacement values and can also graphically display the test.

Assouline Compressor type 1.5 HP.

Fluid dispensing system Model 1500XL.

Procedure:

The balloon was inserted into a 3-mm glass tube, at straight position or inclined to 45°. A guidewire was inserted into the inner tube in order to stabilize the folding motion. The balloon was inflated using a compressor and the inflation pressure was controlled by a dispenser. The procedure was performed at pressures ranging between 3-7 atm, with increments of 1 atm. The balloon was folded using the Hounsfield Test machine, by pulling the inner tube at speed of 100 mm/min up to 20 mm, and then pushing back at the same speed until the balloon was completely unfolded.

Four tests were conducted at each pressure, to confirm that the results could be replicated.

Results:

The maximal force required for folding the balloon at each pressure is presented in FIG. 10. The maximal force increases with the inflation pressure for both positions (straight and inclined) and ranges between 2-3.5 N (200-350 gr) with increments vary between 0.2-0.4 N (20-40 gr) per step of 1 atm in pressure. Higher inflation pressure requires greater force to fold the balloon. The relationship is approximately linear ($R^2$=0.98). The maximal forces are slightly lower for the inclined position; however, repeated tests at the straight position revealed that the lesser forces result from the material fatigue. To support this assumption, visual examination of the balloon after 40 repeats showed that the balloon material lost its flexibility and looked crumpled.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

What is claimed is:

1. A rapid exchange balloon catheter comprising:

an outer conduit having a wall;

an inner conduit having a proximal end and a distal end and a lumen, said inner conduit is suitable for total or partial passage over a guide wire, wherein said proximal end of said inner conduit is angled such that it pierces said wall of said outer conduit and is fixedly and sealingly attached to said wall of said outer conduit to provide a lateral port in said out conduit for insertion of said guide wire into said lumen of said inner conduit;

a slidable intermediate tube movably and slidably disposed between said outer conduit and said inner conduit, said intermediate tube has a proximal end and a distal end, said proximal end of said intermediate tube is a closed end that sealingly and slidably passes through an opening disposed at the proximal end of said outer conduit, said proximal end of said intermediate tube is a sealed end that extends proximally beyond said opening disposed at the proximal end of said outer conduit, said intermediate tube has a lateral elongated opening therein, wherein the angled proximal part of said inner conduit passes through and is disposed within said lateral elongated opening of said intermediate tube such that said slidable intermediate tube may be axially moved proximally and distally within said outer conduit without hindrance from said angled proximal part of said inner conduit;

an inflatable intussusceptable balloon having a proximal balloon margin sealingly attached to the surface of a distal tip of said outer conduit and a distal balloon margin sealingly attached to a surface of the distal end of said slidable intermediate tube, said inflatable balloon is configured to intussuscept upon sliding of said slidable intermediate tube in a proximal direction and to form a distal and/or proximal open cavity within said balloon; and a fluid port formed in said outer conduit for the introduction of an expansion fluid into the lumen of the balloon, and for the removal of the expansion fluid from a lumen of said balloon.

2. The rapid exchange balloon catheter according to claim 1, wherein the catheter is characterized by its ability to withstand pressure values in the range of 0-25 atmospheres developing within the catheter at various stages of its operation.

3. The rapid exchange balloon catheter according to claim 1, wherein the rapid exchange catheter further includes a pressure regulating mechanism in fluidic communication with the lumen of the outer conduit for reducing or preventing excessive pressure within the lumen of the outer conduit and within the balloon upon proximal axial movement of the slidable intermediate tube in relation to the outer conduit and the intussuscepting of the balloon.

4. The rapid exchange balloon catheter according to claim 3, wherein the pressure regulating mechanism
comprises a discharge valve in fluidic communication with the lumen of the outer conduit for reducing the pressure of inflation fluid within the lumen of the outer conduit whenever the pressure within the catheter exceeds a threshold value.

5. The rapid exchange balloon catheter according to claim 4, wherein the pressure threshold value of the discharge valve is in the range of 5-20 atmospheres.

6. The rapid exchange balloon catheter according to claim 1, wherein the balloon is characterized by having, in its inflated state, a shape which is capable of guiding the intussuscepting of the distal and/or proximal portion(s) thereof upon proximal movement of the slidable intermediate tube in relation to the outer conduit.

7. The balloon catheter according to claim 6, wherein the balloon is characterized by having, in its inflated state, a distal taper with a rounded distal extremity.

8. The balloon catheter according to claim 1, wherein the inner conduit, the outer conduit and the slidable intermediate tube are characterized by their ability to withstand axially directed forces in the range of between 2 and 20 Newton without undergoing deformation.

9. The balloon catheter according to claim 1, wherein the catheter also includes a lubricant to facilitate the sliding of the slidable intermediate tube along the inner conduit.

10. The balloon catheter according to claim 1, wherein the balloon has a burst pressure within the range of 12-20 atmospheres.

11. The balloon catheter according to claim 1, wherein the catheter also includes a stent mounted on the balloon.

12. A method for collecting and/or removing debris from an internal passage of a mammal, the method comprising the steps of:
a) inserting a rapid exchange balloon catheter into said internal passage, said rapid exchange catheter comprises an outer conduit having a wall, an inner conduit having a proximal end and a distal end and a lumen, said inner conduit is suitable for total or partial passage over a guide wire, said proximal end of said inner conduit is angled such that it pierces said wall of said outer conduit and is fixedly and sealingly attached to said wall of said outer conduit to provide a lateral port in said outer conduit for insertion of said guide wire into said lumen of said inner conduit, a slidable intermediate tube movably and slidably disposed between said outer conduit and said inner conduit, said intermediate tube has a proximal end and a distal end, said proximal end of said intermediate tube is a closed end that sealingly and slidably passes through an opening disposed at the proximal end of said outer conduit, said proximal end of said intermediate tube is a sealed end that extends proximally beyond said opening disposed at the proximal end of said outer conduit, said intermediate tube has a lateral elongated opening therein, wherein the angled proximal part of said inner conduit passes through and is disposed within said lateral elongated opening of said intermediate tube such that said slidable intermediate tube may be axially moved proximally and distally within said outer conduit without hindrance from said angled proximal part of said inner conduit, an inflatable intussusceptable balloon having a proximal balloon margin sealingly attached to the surface of a distal tip of said outer conduit and a distal balloon margin sealingly attached to a surface of the distal end of said slidable intermediate tube, said inflatable balloon is configured to intussuscept upon sliding of said slidable intermediate tube in a proximal direction and to form a distal and/or proximal open cavity within said balloon, and a fluid port formed in said outer conduit for the introduction of an expansion fluid into the lumen of the balloon, and for the removal of the expansion fluid from a lumen of said balloon;
b) advancing said catheter until a distal end thereof has reached a site, at which it is desired to collect and/or trap debris;
c) inflating said balloon with expansion fluid;
d) moving said slidable intermediate tube in a proximal direction, such that the distal and/or proximal end(s) of said balloon intussuscept (s) to form a cavity within said balloon;
e) deflating said balloon, to enlarge said cavity into which said debris is collected and entrapped; and
f) removing said balloon catheter from said internal passage of said mammal, together with said entrapped debris.

13. The method according to claim 12, wherein the internal passage is a blood vessel.

14. The method according to claim 12, wherein said step (b) of inflating also includes deploying a stent mounted on said balloon.

15. The method according to claim 12 wherein said catheter further includes a discharge valve in fluidic communication with said lumen of said outer conduit, and wherein the method also includes the step of discharging expansion fluid from said discharge valve whenever the pressure within said catheter exceeds a threshold value.

16. The method according to claim 15, wherein said pressure threshold value is in the range of 5-20 atmospheres.

17. The method according to claim 12, wherein said step of inflating comprises inflating said balloon at a pressure of up to 20 atmospheres.

18. The method according to claim 13, wherein said blood vessel is a constricted blood vessel and wherein the step of inflating also comprises inflating said balloon to dilate said constricted blood vessel.

19. The method according to claim 12, further including the step of inserting an interventional tool through the lumen of said inner conduit for treating said internal passage.

20. The method according to claim 12, wherein said step of inserting comprises passing said catheter over a guide wire inserted into said internal passage.

* * * * *